US006699207B2

(12) United States Patent
Tasch et al.

(10) Patent No.: US 6,699,207 B2
(45) Date of Patent: Mar. 2, 2004

(54) METHOD AND APPARATUS FOR DETECTING LAMENESS IN ANIMALS

(75) Inventors: Uri Tasch, Baltimore, MD (US); Benny Erez, Silver Spring, MD (US); Alan M. Lefcourt, Elkridge, MD (US); Mark Varner, New Carrollton, MD (US)

(73) Assignee: University of Maryland, Baltimore, MD (US)

( * ) Notice: Subject to any disclaimer, the term of this patent is extended or adjusted under 35 U.S.C. 154(b) by 70 days.

(21) Appl. No.: 09/827,311

(22) Filed: Apr. 6, 2001

(65) Prior Publication Data

US 2002/0055691 A1 May 9, 2002

Related U.S. Application Data

(60) Provisional application No. 60/207,823, filed on May 30, 2000.

(51) Int. Cl.[7] ............................ A61B 5/103; A61B 5/117
(52) U.S. Cl. ......................................................... 600/587
(58) Field of Search ................................ 600/587, 592; 73/865.4, 379.08, 862.041, 862.641, 172; 128/905; 340/573.1, 666

(56) References Cited

U.S. PATENT DOCUMENTS

| 4,122,840 A | * | 10/1978 | Tsuchiya et al. ............. 600/592 |
| 4,195,643 A | * | 4/1980 | Pratt, Jr. ...................... 600/592 |
| 5,186,062 A | * | 2/1993 | Roost ......................... 73/865.4 |
| 5,299,454 A | * | 4/1994 | Fuglewicz et al. ............. 73/172 |
| 5,736,656 A | | 4/1998 | Fullen et al. |
| 5,987,982 A | | 11/1999 | Wenman et al. |

OTHER PUBLICATIONS

Rajkondawar, Parimal, Development of a Reaction Force Detection System that Detects Lameness and Assesses it Severity in Dairy Cattle, Department of Mecahnical Engineering, UMBC, pp. 1–3.*

Zhang et al, Mechanical Characteristics of Bovine Hooves: Comparing Healthy and Ailing Hooves, Abstract.*

"A Lameness Scoring System That Uses Posture and Gait to Predict Dairy Cattle Reproductive Performance", D.J. Sprecher et al., Theriogenology—An International Journal of Animal Reproduction, Apr. 15, 1997, vol. 47, No. 6, pp. 1180–1187.

"The Way Cattle Walk" Steps Toward Lameness Management, H.R. Whay et al., Cattle Practice, vol. 7, Part 4, BCVA 1999.

"Lameness in Cattle", Paul R. Greenough et al., Wright—Scientechnica 1981, pp. 1–9.

"Modifications of a force plate system for equine gait analysis", Janet E. Steiss et al., American Journal of Veterinary Research, vol. 43, Mar. 1982, pp. 538–540.

"Accuracy of Determining the Point of Force Application With Piezoelectric Force Plates", Maarten F. Bobbert et al., Journal of Biomechanics, vol. 23, No. 7, 1999, pp. 705–710.

"Relationships between ground reaction force patterns and kinematics in the walking and trotting horse", H.W. Merkens et al., Animal Locomotion, Equine Veterinary Journal, 1994, pp. 67–70.

(List continued on next page.)

*Primary Examiner*—Max F. Hindenburg
*Assistant Examiner*—Brian Szmal
(74) *Attorney, Agent, or Firm*—McDermott, Will & Emery

(57) ABSTRACT

A computer-based diagnostic system is provided to detect and analyze ground reaction forces produced by an animal passing through the diagnostic system, and includes, in one aspect, a first plate and a second plate disposed adjacent the first plate, a first plurality of load cells, and a second plurality of load cells. Each of the first and second plurality of load cells are configured to detect, respectively, a force applied to the first plate and the second plate along at least one axis and output signals representative of the detected force. A processor is provided to execute at least one force analysis instruction set, whereby the force analysis instruction set receives the signals output from the first and second plurality of load cells and calculates, a magnitude and location of a force applied to either of the first plate and the second plate.

94 Claims, 21 Drawing Sheets

OTHER PUBLICATIONS

"Kinetics and kinematics of the equine hind limb: In vivo tendon loads and force plate measurements in ponies", Dirk J. Riemersma et al., American Journal of Veterinary Research, vol. 49, No. 8, Aug. 1988, pp. 1344–1352.

"Limb Locomotion—speed distribution analysis as a new method for stance phase detection", C. Peham et al., Journal of Biomechanics 32, 1999, pp. 1119–1124.

"A Method of Signal Processing in Motion Analysis of the Trotting Horse", C. Peham et al., Journal of Biomechanics, vol. 29, No. 8, 1996, pp. 1111–1114.

"Objective determination of ground contact of equine limbs at the walk and trot: comparison between ground reaction forces, accelerometer data and kinematics", H.C. Schamhardt et al., Equine Veterinary Journal, 1994, pp. 75–79.

"Contributions to variance in force–plate analysis of gait in dogs", D.J. Jevens et al., American Journal of Veterinary Research, vol. 54, No. 4, Apr. 1993, pp. 612–615.

"A review of research on equine locomotion and biomechanics", D.H. Leach et al., Equine Veterinary Journal, vol. 15, No. 2, 1983, pp.93–102.

McPhail Chair Abstracts, three articles by H.M. Clayton et al.

"Force plate analysis of the walking gait in healthy dogs", Steven C. Budsberg et al., American Journal of Veterinary Research, vol. 48, No. 6, Jun. 1987, pp. 915–918.

"Investigating locomotion of dairy cows by use of high speed cinematography", A.H. Herlin et al., Equine Veterinary Journal Suppl. 23, 1997, pp. 106–109.

"Effects of subject stance time and velocity on ground reaction forces in clinically normal Greyhounds at the trot", Ronald M. McLaughlin, Jr. et al., American Journal of Veterinary Research, vol. 55, No. 12, Dec. 1994, pp. 1666–1671.

"Genetic Analysis of Clinical Lameness in Dairy Cattle", P.J. Boettcher et al., Journal of Dairy Science, vol. 81, No. 4, 1998, pp. 1148–1156.

"Automatic Weighing of Dairy Cows", U.M. Peiper et al., Journal of Agricultural Engineering Research, 1993, pp. 13–24.

"Lameness and Hoof Health", Steven L. Berry, Animal Health, www.dairybuz.com/archieve/a_health_35.htm., Aug. 1999, pp. 1–7.

"The Science of Evaluating Lameness and Pain Relief", Brian S. Beal et al., Pfizer Animal Health, 1999.

"Vertical ground reaction force distribution during experimentally induced acute synovitis in dogs", Paul F. Rumph et al., American Journal of Veterinary Research, vol. 54, No. 3, Mar. 1993, pp. 365–369.

"Prevalence and severity of lameness in lactating dairy cows in a sample of Minnesota and Wisconsin herds", S.J. Wells et al., Journal of the American Veterinary Medical Association, vol. 202, No. 1, Jan. 1993, pp. 78–82.

"How to use footbaths to prevent lameness", How–to–series, Dairy Herd Management, May 1986, pp. 16–17.

"Effects of lameness on the behaviour of cows during the summer", S.A. Hassall et al., The Veterinary Record, Jun. 5, 1993, pp. 578–580.

"The association between lameness and fertility in dairy cows", S. Lucey et al., The Veterinary Record, Jun. 7, 1986, pp. 628–631.

"Why neglect the lame cow?" and "Associations between types of lameness and fertility", D.W.Collick et al., Veterinary Record, vol. 125, No. 5, Jul. 29, 1989, pp. 102–106.

"Lameness in dairy cows and farmers' knowledge, training and awareness", J.M. Mill et al., The Veterinary Record, Feb. 12, 1994, pp. 162–164.

"Laminitis in Cattle", David A. Morrow, Veterinary Medicine/Small Animal Clinician, Feb. 1966, pp. 138–146.

"Lameness in Dairy Cattle", Gerald Stokka et al., Kansas State University Research and Extension, MF–2070, Jan. 1997.

"Quantification of Equine Ground Reaction Force Patterns", H.C. Schamhardt et al., Journal of Biomechanics, vol. 20, No. 4, 1987, pp. 443–446.

"The Influence of Dietary protein Intake and of Hoof Trimming on Lameness in Dairy Cattle", F.J. Manson et al., British Society of Animal Production, 1988, pp. 191–199.

"An Epidemiological Study of Dairy Cattle Lameness", M.J. Clarkson et al., Society for Veterinary Epidemiology and Preventive Medicine, Proceeding of a meeting held Mar. 31–Apr. 2, 1993, pp. 87–95.

Changes in Limb Loading With Lameness for a Number of Friesian Cattle, G.B. Scott, The British Veterinary Journal, 1989, pp. 29–38.

"A Dynamic Force and Moment Analysis System for Brachiation", Y.H. Chang et al., The Journal of Experimental Biology 200, 1997, pp. 3013–3020.

"Multiple Force Platform Analysis of the Canine Trot: a New Approach to Assessing Basic Characteristics of Locomotion", J.E.A. Bertram et al., Vet Comp Orthop Traumatol, 1997, pp. 44–53.

"Disease–specific changes in equine ground reaction force data documented by use of principal component anaylis", G.E. Williams et al., American Journal Veterinary Research, vol. 60, No. 5, May 1999, pp. 549–555.

"Investigating the Effect of Gait on the Ground Reaction Forces of Running", A.C. Rowat.

"Force Plate Studies of Equine Biomechanics", G.W. Pratt et al., American Journal of Veterinary Research, vol. 37.

"Understanding Herd Lameness A Worthwhile Investment. Recognizing the Problem and its Cause", Paul R. Greenough, pp. 334–349.

"Behaviour of lame and normal dairy cows in cubicles and in a straw yard", S.S. Singh et al., Veterinary Record, 1993, pp. 204–208.

"Force Plate Analysis: A Noninvasive Tool for Gait Evaluation", Mark A. Anderson et al., Compendium on continuing Education, Jul. 1994, pp. 857–864.

"Footswitch System For Measurement of the Temporal Parameters of Gait", Jeffrey M. Hausdorff et al., Journal of Biomechanics, vol. 28, No. 3, 1995, pp. 347–351.

"Methods, Applications and Limitations of Gait Analysis in Horses", E. Barrey, The Veterinary Journal vol. 157, pp. 7–22.

"Decomposition of Superimposed Ground reaction Forces Into Left and Right Force Profiles", Brian L. Davis et al., Journal of Biomechanics, vol. 26, pp. 593–597.

"Some New Ideas on an Old Problem—A UK Vets View of Lameness", Roger Blowey, Ontario Dairy Symposium 7, pp. 133–143.

"Foot Health From a Veterinarian's Perspective", J.K. Shearer, Paper from University of Florida, College of Veterinary Medicine.

"An Introduction to the Kaegi Equine Gait Analysis System in the Horse", J.A. Auer et al., pp. 209–226.

"Locomotion analysis technology for evaluation of lameness in horses", D.H. Leach, Equine Veterinary Journal, 1987, pp. 97–99.

* cited by examiner

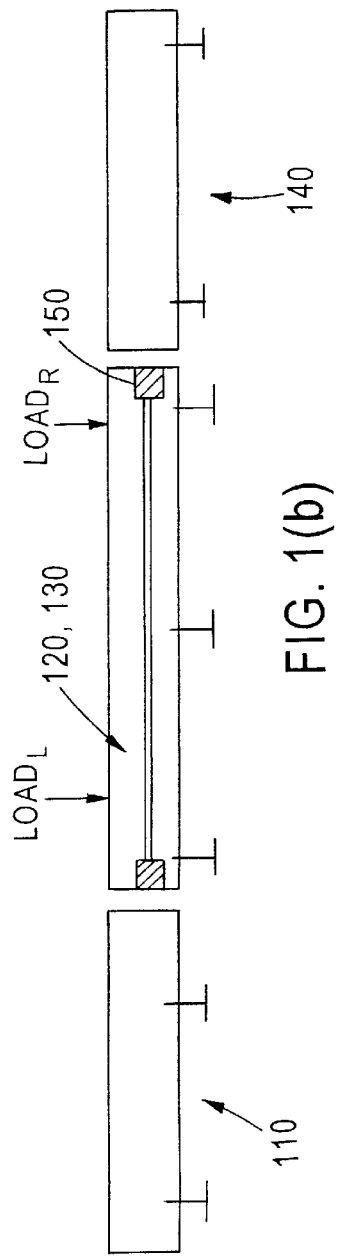
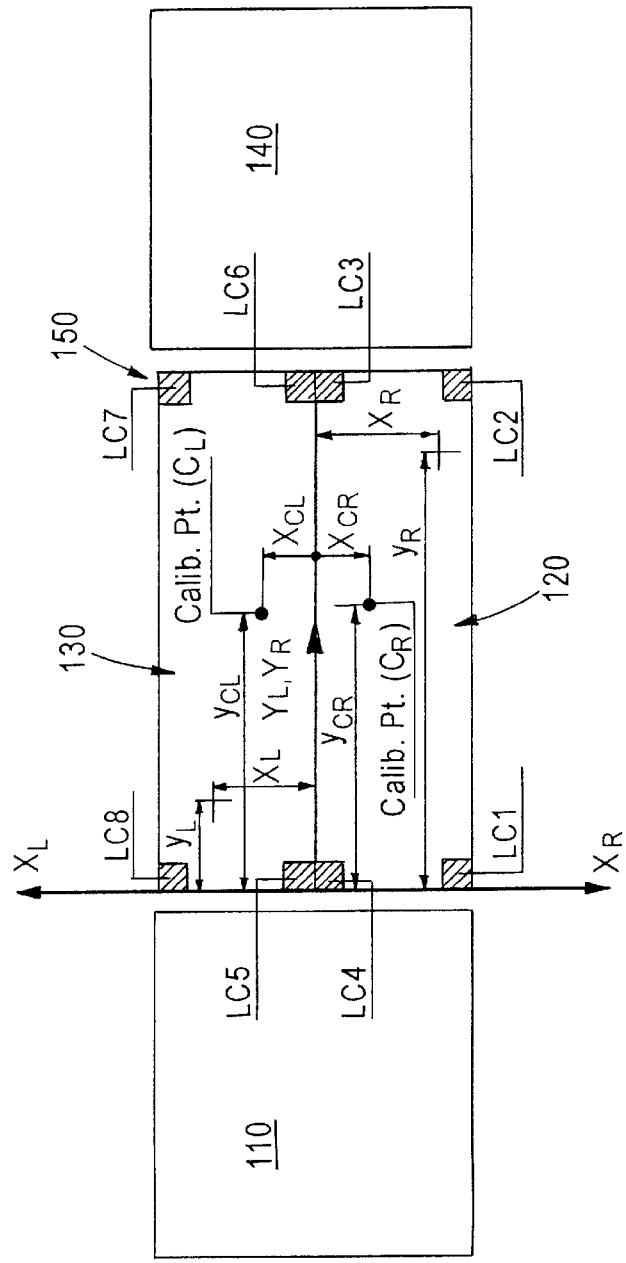
FIG. 1(b)
FIG. 1(c)

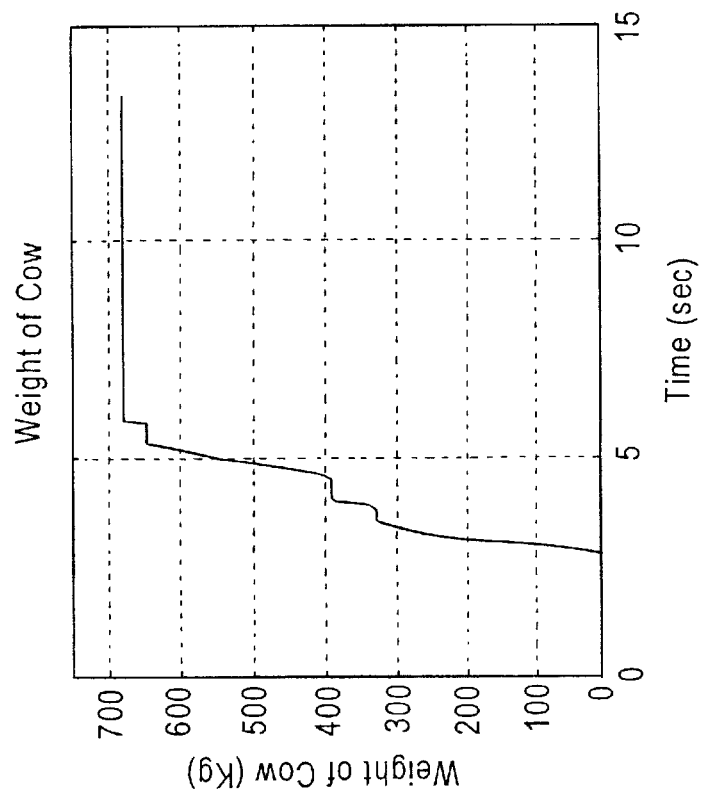
FIG. 2(iv) Weight of Cow
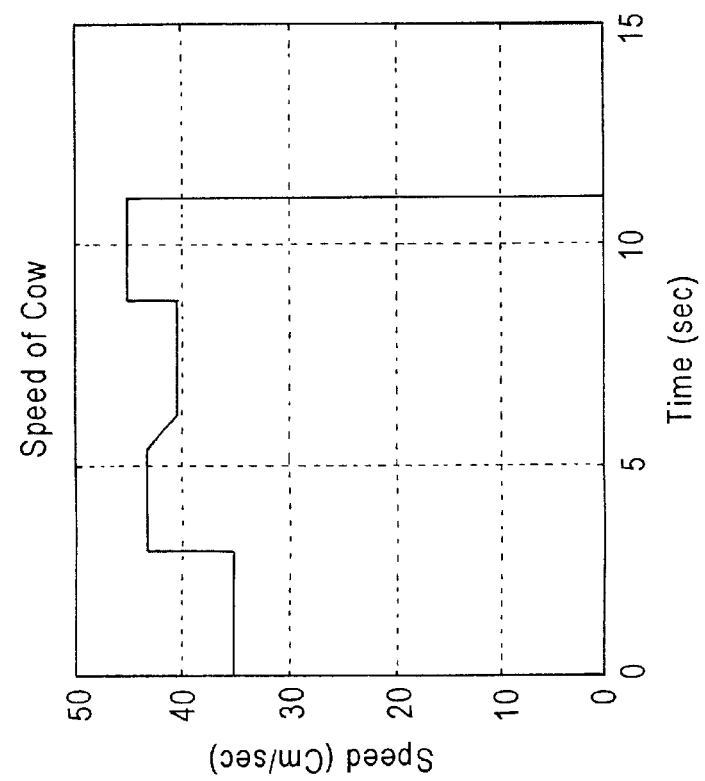
FIG. 2(iii) Speed of Cow

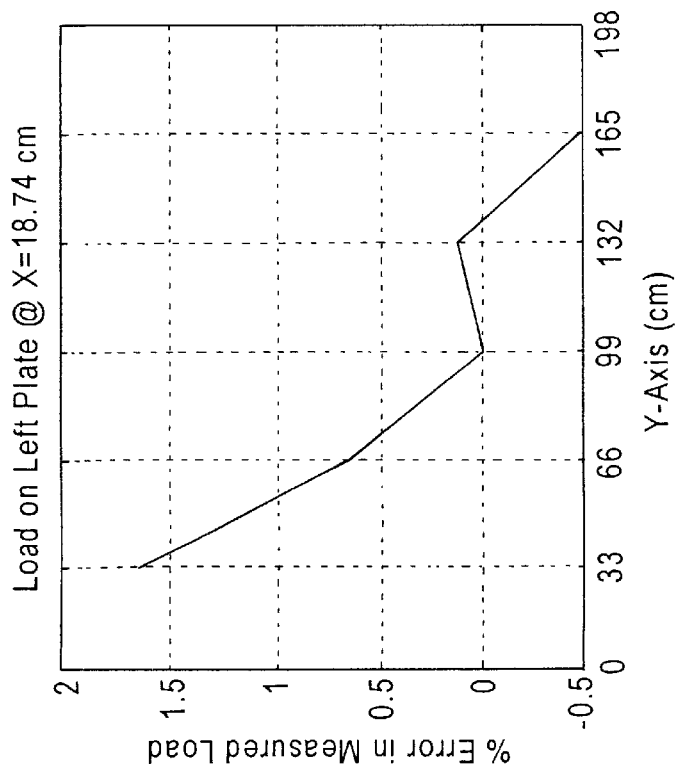
FIG. 3(iii)

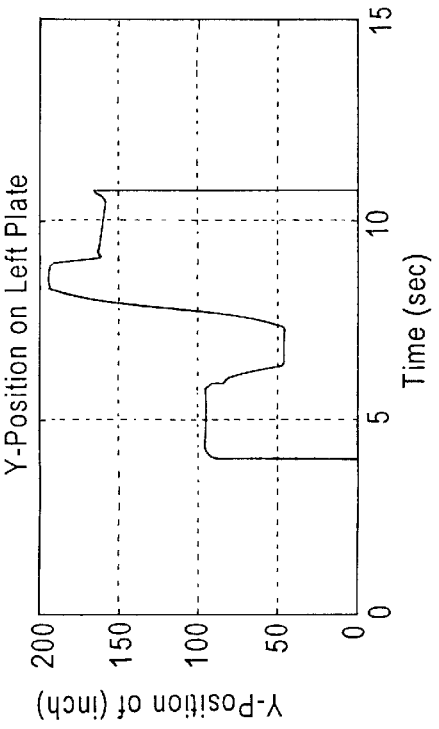
FIG. 4(iii)

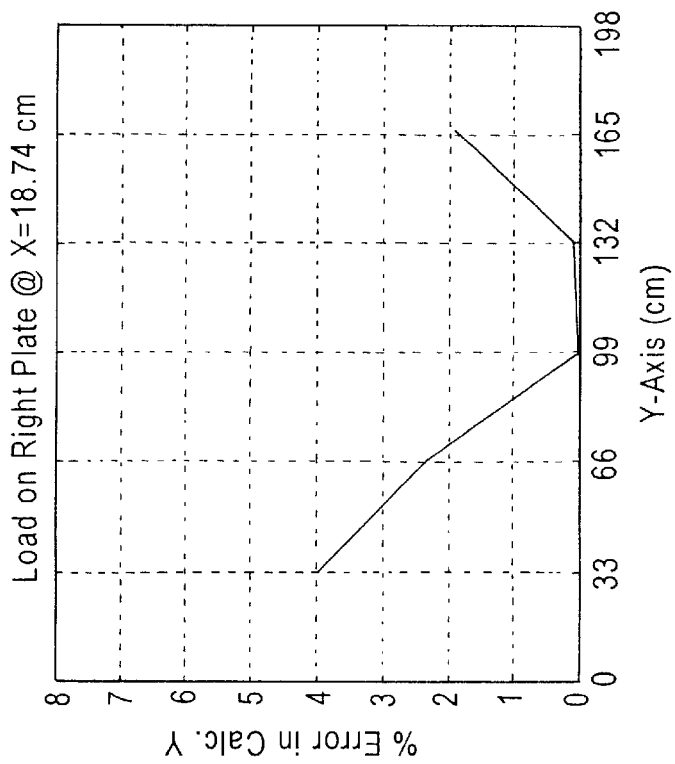
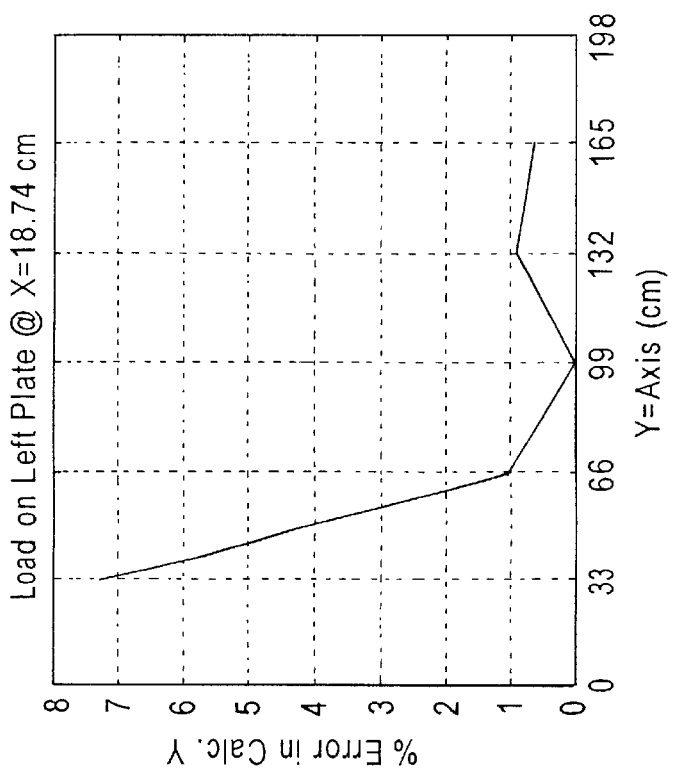

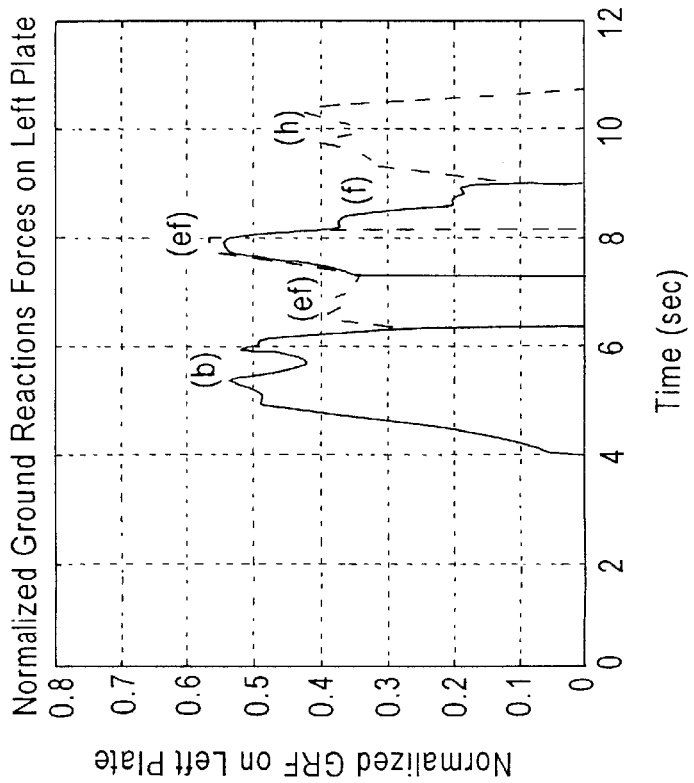
FIG. 6(iii)

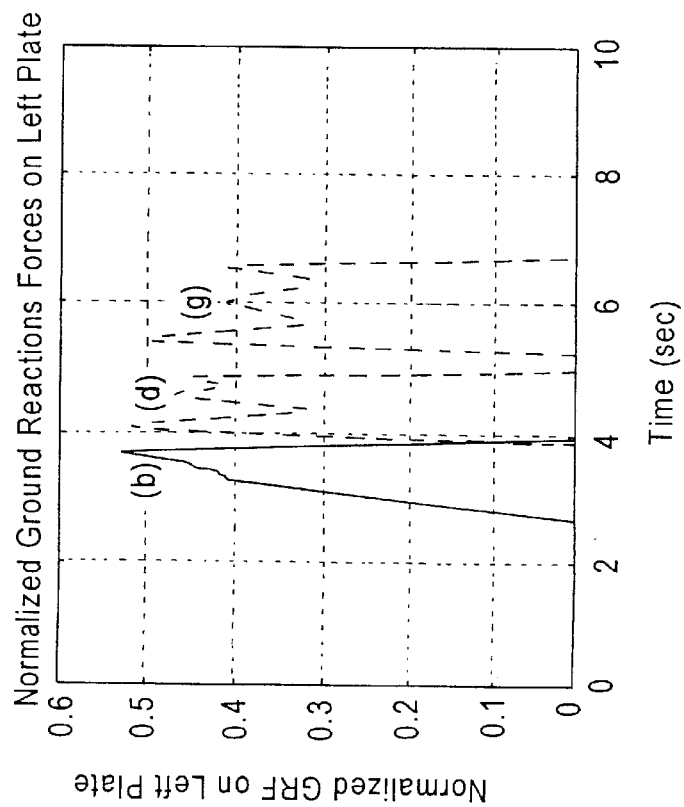
FIG. 7(iii)

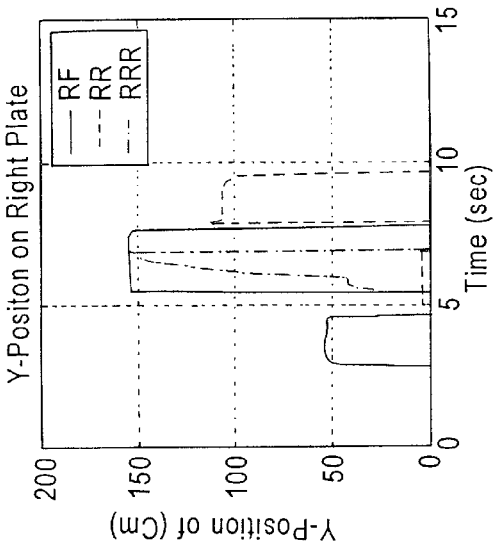
FIG. 8(a) Y-Position on Left Plate
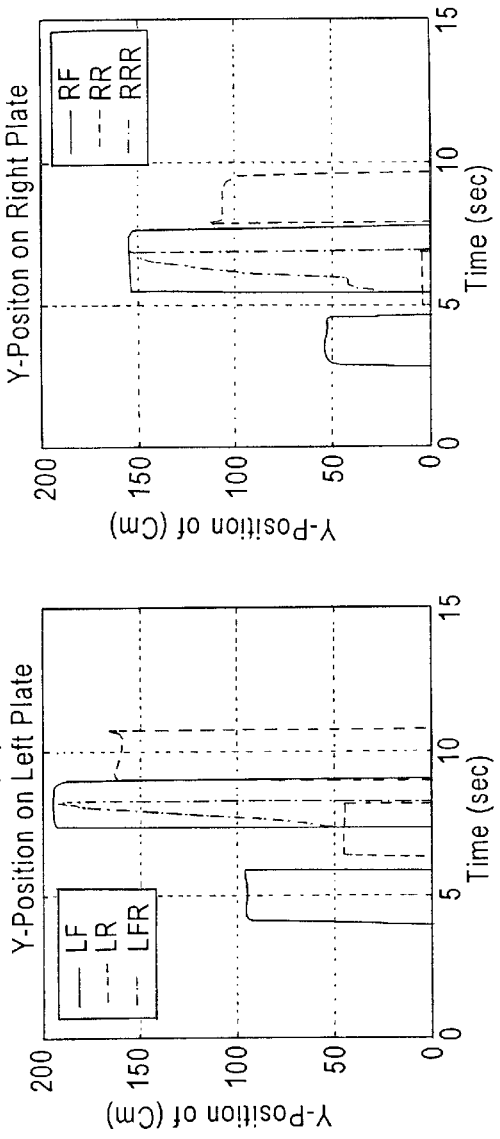
FIG. 8(b) Y-Position on Right Plate
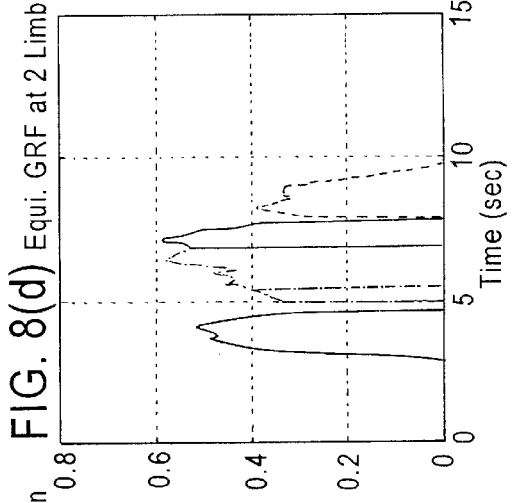
FIG. 8(c) Equi. GRF at 2 Limb Position
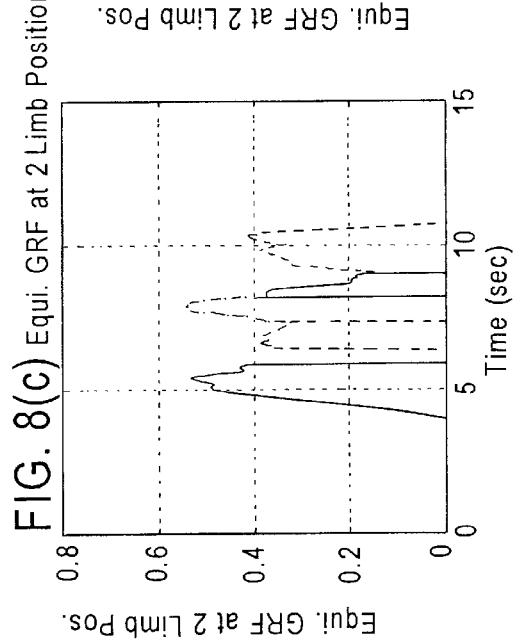
FIG. 8(d) Equi. GRF at 2 Limb Position

Limb movement variables of Individual Limbs of Sound Cows 973 and 984

| Limb Movement Variables | Sound Cow 973 | | | | Sound Cow 984 | | | |
|---|---|---|---|---|---|---|---|---|
| | Left Front [LF] | Right Front [RF] | Left Rear [LR] | Right Rear [RR] | Left Front [LF] | Right Front [RF] | Left Rear [LR] | Right Rear [RR] |
| Normalized PGRF | 0.49 | 0.52 | 0.39 | 0.51 | 0.56 | 0.59 | 0.41 | 0.44 |
| Stance time (sec) | 1.00 | 0.89 | 1.00 | 0.97 | 1.11 | 1.10 | 0.92 | 1.10 |
| Impulse (sec) | 0.34 | 0.33 | 0.30 | 0.35 | 0.40 | 0.40 | 0.26 | 0.31 |
| Normalized AGRF | 0.34 | 0.37 | 0.30 | 0.36 | 0.36 | 0.36 | 0.28 | 0.29 |
| Step size (cm) | NA | NA | NA | NA | NA | 114 | NA | 117 |
| Energy (1/sec) | 0.47 | 0.47 | 0.37 | 0.40 | 0.54 | 0.55 | 0.41 | 0.35 |
| P-energy (1/sec$^2$) | 4.51 | 4.70 | 3.32 | 3.34 | 5.15 | 5.32 | 3.77 | 2.81 |

FIG. 11

Limb movement variables of Individual Limbs of Lame Cows 113 and 982

| Limb Movement Variables | Lame Cow 113 | | | | Lame Cow 982 | | | |
|---|---|---|---|---|---|---|---|---|
| | Left Front [LF] | Right Front [RF] | Left Rear [LR] | Right Rear [RR] | Left Front [LF] | Right Front [RF] | Left Rear [LR] | Right Rear [RR] |
| Normalized PGRF | 0.47 | 0.53 | 0.19 | 0.41 | 0.55 | 0.57 | 0.36 | 0.27 |
| Stance time (sec) | 2.00 | 1.40 | 1.05 | 1.50 | 1.14 | 0.97 | 1.27 | 0.99 |
| Impulse (sec) | 0.67 | 0.44 | 0.11 | 0.53 | 0.40 | 0.35 | 0.33 | 0.16 |
| Normalized AGRF | 0.33 | 0.32 | 0.10 | 0.36 | 0.35 | 0.36 | 0.26 | 0.17 |
| Step size (cm) | 84 | NA | 117 | NA | 96 | 102 | 92 | 142 |
| Energy (1/sec) | 0.41 | 0.33 | 0.12 | 0.33 | 0.46 | 0.54 | 0.30 | 0.20 |
| P-energy (1/sec$^2$) | 3.74 | 1.44 | 1.04 | 2.20 | 4.50 | 5.14 | 2.55 | 1.40 |

FIG. 12

METHOD AND APPARATUS FOR DETECTING LAMENESS IN ANIMALS

This application claims the benefit of provisional application No. 60/207,823 filed May 30, 2000.

BACKGROUND OF INVENTION

This invention relates to a new method and apparatus for detecting lameness in animals and promoting animal well-being. The preferred embodiment of this invention is for detecting lameness in four legged animals, such as but not limited to horses, dairy cows, non-dairy cows, pigs, and sheep.

Dairy production is an important industry in the U.S. and a major branch of agriculture in many countries around the world. Cow lameness caused by hoof and leg ailments is a costly problem for the dairy farmer. Lameness necessitates medical treatment, reduces milk production, results in decreased body condition, impairs reproduction performance, and adversely impacts the social status of animals. Economically, lameness is reported to be the third most costly problem for dairy herds following mastitis and sub-fertility. The average cost of lameness is reported to be 412 dollars per incident and the annual incidence rate in the U.S. is fifteen percent. Thus, the annual economic losses due to lameness is over 570 million dollars for the over nine million U.S. cows. These losses significantly impair dairy farms and harm the entire bovine industry.

In addition to the economic impact, lameness is also recognized as an important animal welfare issue. The 1993–94 Annual Report of the Animal Welfare Foundation of the British Veterinary Association states that ". . . if it were possible to substantially reduce the incidence of lameness, this single initiative, more than any other would benefit more animals than any other (initiative) . . . ." Thus, researchers have focused on developing a means of detecting hoof and leg ailments at their early onset.

Lameness in dairy herds has been reported to be a critical economic factor and a vital animal-welfare issue for the dairy industry around the world. Various lameness evaluation schemes that assess the severity of the ailment, using non-clinical personal, have been suggested. These schemes are based on visual observations of individual cattle. In one scheme, lameness scoring is based on the shape of the cow's back both as the animal stands and as the animal walks. However, although this scheme lends itself to field use, its results are highly subjective and are non-quantitative in nature.

There are reports of management programs to control lameness and studies of the housing factors that influence the locomotion of dairy cows. Some of the etiological factors contributing to lameness are nutrition, bacterial and fungal infections, bacterial endotoxin, environmental conditions, housing, flooring, feeding management, and cow behaviors. The fact that many different factors lead to lameness makes it almost impossible to eliminate hoof and leg ailments and imposes difficulties for diagnostic procedures. Early detection of hoof and leg ailments is not a yet reality and most farmers record an incidence of lameness only at the stage when the cow is crippled. Thus, there is a need in the art for a method and an apparatus able to provide early detection of hoof and leg problems, which will enable prompt veterinarian medical intervention to reduce economic losses, lessen the pain that the animal endures, and expedite the animal's recovery process. Furthermore, an early detection system will facilitate scientific testing of management programs designed to reduce the rate of incidence of lameness in dairy herds and will promote animal well-being.

A research effort that analyzes the gait of horses and detects lame limbs is reported in Schamhardt, H. C. and Merkens, H. W., "Objective determination of ground contact of equine limbs at the walk and trot: comparison between ground reaction forces, accelerometer data and kinematics," *Equine Vet. J Suppl*. No. 17, pp. 75–79, 1994. In this study, the animal is led over a single force plate and a Horse ("H") index is calculated. However, this method and apparatus only detected the force of one of the animal's limbs. To obtain forces from each of the animal's limbs, four separate tests would have to be performed. Therefore, even though a set of forces could be obtained for each limb, such data was merely a compilation of four or more separate tests wherein the speed of the animal, as well as other variables, varied in each run. To detect lameness, the H value is compared with a previously calculated sound horse model. This type of system and index are not available for detecting lameness in dairy cows and they are not as sensitive and versatile as the system described herein. In particular, the H index relies on leading a horse multiple times across a measuring device under the assumption that the speed of the horse remains constant during all measurements.

SUMMARY OF INVENTION

This invention relates to a method and apparatus for detecting lameness in animals and for promoting animal well-being, wherein one or more force places are configured to detect forces generated by an animal and these forces are utilized to determine the soundness of an animal.

Additional advantages and other features of the present invention will be set forth in part in the description which follows and in part will become apparent to those having ordinary skill in the art upon examination of the following or may be learned from the practice of the invention. The advantages of the invention may be realized and obtained as particularly pointed out in the appended claims.

In one aspect, the invention comprises a computer-based diagnostic system to detect and analyze ground reaction forces produced by an animal passing through the diagnostic system, comprising a first plate and a second plate disposed adjacent the first plate. A first plurality of load cells is also provided, wherein each of the first plurality of load cells is configured to detect a force applied to the first plate along at least one axis and output at least one signal representative of the detected force. Similarly, a second plurality of load cells is provided, wherein each of the second plurality of load cells is configured to detect a force applied to the second plate along at least one axis and output at least one signal representative of the detected force. A processor adapted to execute at least one force analysis instruction set is provided to, in combination with the force analysis instruction set, receive signals output from the first and second plurality of load cells and calculate a magnitude and location of a force applied to each of the first plate and the second plate. In another aspect of this diagnostic system, a length each of the first plate and the second plate is selected to be greater than a distance traversed by the animal at a standard walking gait of the animal so that each limb of the animal contacts a respective one of the first plate and second plate at least once. In other words, this aspect of the invention permits all measurements to be made during a single pass of the animal through the system thereby ensuring that all measurements are made at a single transversal speed. Other aspects of the invention include incorporation of speed sensors to obtain the average or instantaneous speed(s) of an animal through the system.

In another preferred aspect, the invention comprises a computer-based method for detecting and analyzing ground reaction forces produced by an animal, comprising the steps of guiding an animal to move across an instrumented force-sensing floor comprising a left floor plate, a right floor plate, a plurality of left floor plate load cells configured to measure a force applied to the left floor plate and output a force proportioned signal, and a plurality of right floor plate load cells configured to measure a force applied to the right floor plate and output a force proportioned signal; constraining at least one of the animal's lateral body movement and leg movement so that the animal's left limbs contact the left floor plate and the animal's right limbs contact the right floor plate; calculating forces applied to the left floor plate and to the right floor plate by summing the signals output by the left floor plate load cells and right floor plate load cells, respectively; and comparing the calculated forces to a range of forces indicative of at least one of a sound animal condition, an indeterminate animal condition, or a lame animal condition.

Still another aspect of the invention includes a computer-readable medium bearing instructions enabling a computer having at least one processor to detect and analyze ground reaction forces produced by an animal to determine a physical condition of the animal, the instructions, when executed by a computer, causing the computer to carry out the steps of calculating ground reaction forces produced by the animal by summing the force proportioned signals output by load cells separately measuring loads of each of a left floor plate and a right floor plate and comparing the calculated forces to a range of forces indicative of at least one of a sound animal condition, an indeterminate animal condition, or a lame animal condition.

BRIEF DESCRIPTION OF THE FIGURES

FIG. 1(b) is an isometric view of a force plate used in the present invention and an applied load.

FIG. 1(c) is a top down view of the RFD system including a step up, force-detecting floor plates, and ramp down of the present invention.

FIGS. 8(a)–8(f) are graphs showing the Y-positions of the limbs on the left plate (a) and right plate (b), as well as the distributions of an equivalent GRF for two-limb conditions (c and d) and distributions of equivalent GRF to individual limbs (e and f).

FIG. 11 illustrates limb movement variables of individual limbs of two sound cows calculated in accord with the apparatus and method of the invention.

FIG. 12 illustrates limb movement variables of individual limbs of two lame cows calculated in accord with the apparatus and method of the invention.

DETAILED DESCRIPTION OF THE INVENTION

The Reaction Force Device (RFD) system 100 measures, among many other variables, the weight and forces related to walking gait of animals. The RFD system 100 has a walk-through layout configured to guide the animals through the RFD one at a time. As the animal passes through the RFD system, stepping on instrumented plates, the animal's limb reaction forces, weight, bilateral symmetry of limb reaction forces, and other factors may be determined, as discussed below. Once one animal has passed through the RFD system, another animal may then enter the RFD system. Thus, the RFD system is particularly suited to applications wherein a plurality of animals, such as a herd of cattle, are sequentially enter the system to determine the presence of lameness in any particular individual in the group.

Figure 1A:
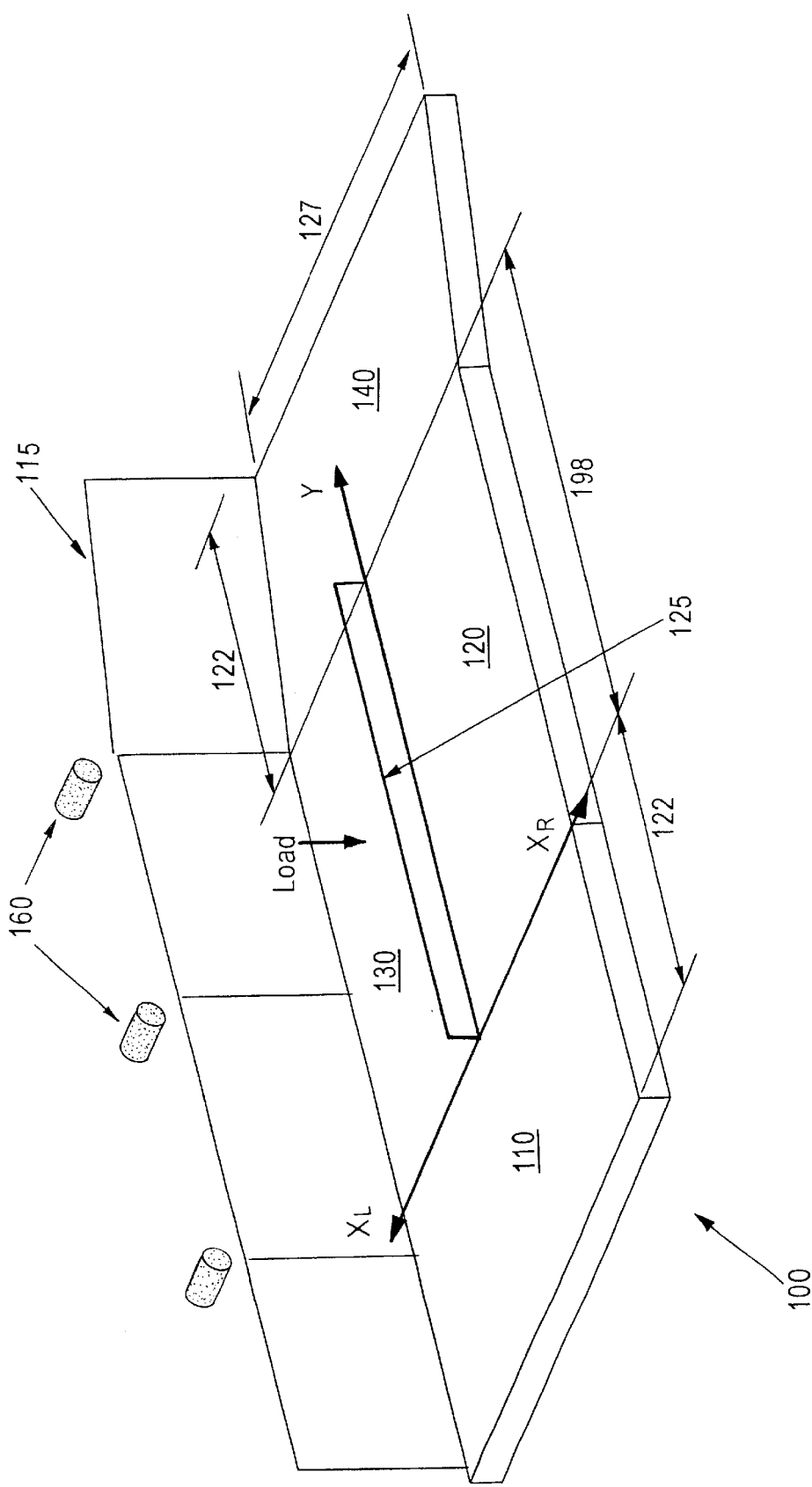
FIG. 1(a) is a schematic representation of Reaction Force Detection (RFD) system of the present invention showing a partial side view of the RFD system including a step up, force-detecting floor plates, and ramp down.

To facilitate sequential movement of a plurality of animals, impediments to animal movement may be provided. In a preferred aspect of the invention, impediments include an initial step-up 110, side railings 115 (shown only on one of two sides in FIG. 1(a)) or side walls that constrain the animal's lateral movement to thereby force the animal to walk over the plate, and a divider 125 the prompts the animal to place its left leg on a left plate 130 and right foot on a right plate 120 or prevents the animal from placing its left leg on a left plate 130 and right foot on a right plate 120. In a preferred aspect, the step-up 110 dimensions are 127 cm×122 cm×18 cm (width, length and height), although these dimensions may be freely varied to accomplish the intended result. The step-up 110 is configured to compel the animals to space themselves and walk through the system one at a time.

Following the step-up 110, animals moving through the RFD system next encounter a floor comprising parallel left and right portions or plates 130, 120 separated by a divider or partition 125 projecting upwardly from a position between the left and right plates, as shown in FIGS. 1(*a*) through 1(*c*). In a preferred aspect, the left and right floor plates 130, 120 are each made of three layers comprising a ³⁄₁₆" steel floor grating covered with ⅛" sheet steel and a top surface comprising an anti-slip, corrosion-resistant flooring. The gratings may be, for example, SGW gratings manufactured by McNichols Corporation of Tampa, Fla. and the anti-slip flooring may be ⅛" Chemplate made by Chemgrate Corporation of Woodinville, Wash.

In a preferred aspect, such as for a bovine application, each plate 130, 120 is 63 cm in width and 198 cm in length, as shown in the central portion of FIG. 1(*a*). As illustrated in FIG. 1(*a*), divider 125 is approximately 1 cm in width, yielding the total width of 127 cm. In an application of the RFD system to horses, for example, it is generally desirable to have a force plate length of between about 300 and 500 cm, although longer force plate lengths could certainly be utilized. It has been determined, however, that if the plate is too small, such as 36 cm×52 cm, data collection of the ground reaction forces (GRFs) for bovines and animals of like gait becomes increasingly difficult, necessitating multiple passes through the system to obtain GRFs for all limbs. Therefore, although the size and number of the plates may be varied in accord with the invention, such variation must permit measurement of the GRFs for all four of the animals limbs in a single pass of the animal through the RFD. This may be accomplished, for example, by sampling the walking gait or other gait such as a trot or run, of a sample population of the animals and determining the distance traversed by the animals at that gait to a desired statistical significance. In one aspect of the invention, it is preferred to use a length inclusive of at least 3 of the distance traversed by the sample population at the desired gait. In another aspect of the invention, the above length is multiplied by a factor such as two, three, or more to obtain multiples of individual limb contact data with the first and second plates 130, 120. Additionally, more than two plates 130, 120 may be used in accord with the invention. For example, another set of plates, a second left plate and a second right plate, could be provided after the first left plate 130 and first right plate 120. Alternatively, prior to or subsequent to the initial plates 130, 120, a fore force plate and a hind force plate could be provided to detect differences in an animal's stance and force distribution between fore limbs and rear limbs.

Partition or divider 125 projects upwardly from an inner edge of one of the left and right plates 130, 120 or a position between the left and right plates. This divider 125, in a preferred aspect of the invention, is a single continuous divider having a width of about 1 cm and a height of between about 0.5 to 1.5 cm. The width and the height may vary in accord with a size of the animal, but is preferred not to exceed a height of about 3 cm. The inventors have determined that barrier 125 heights above 3 cm start to affect the animal's normal cadence, thus potentially reducing the amount of or value of the data obtained. However, in accord with the invention, the height of barrier 125 may exceed 3 cm if the specific data desired to be obtained is not related to or dependent on the animal's cadence and limb cross-over is itself a concern. In a preferred embodiment of the divider 125 may comprise a rigid or semi-rigid material, such as a plastic or resilient rubber, and may preferably be rounded at the edges. A partition or divider 125 is not required, however, as limb-cross over is uncommon and may be corrected by an additional run of the animal through the RFD or by intervention by the RFD user in the data analysis to back out the values of the left limb and right limb, respectively.

As shown by the embodiment of FIG. 1(*c*), each plate 130, 120 is supported by an array of four load cells 150 distributed adjacent the four corners of the respective plate 130, 120. However, this is merely a preferred aspect of the invention. The invention may comprise more or less load cells 150 distributed in various locations and arrangements above, below, or adjacent the plates 130, 120 in accord with the physical configuration and type (e.g., number of axes) of load cell selected and the desired robustness of data.

These load cells 150 measure the ground reaction forces (GRFs) produced as the animal steps on each plate. The RFD system 100 measures these ground reaction forces and calculates the position of the weight placed on the respective floor plate 130, 120. As illustrated in FIG. 1(*c*), each of the plates 130, 120 comprises a separate coordinate system defined by $(X_L, Y_L)$ and $(X_R, Y_R)$, wherein $(X_{L,R}, Y_{L,R})=(0$ cm, 0 cm) is arbitrarily located at the innermost corner of each of the plates 130, 120. In a preferred orientation of the working axes, X is positive in a direction toward the outside of the plates, Y is positive in a direction of the rear or backside of the plates, and Z is positive in an upward direction. The position of a force applied to the plates 130, 120 is thus defined through the left and right coordinate systems $(X_L, Y_L$ and $X_R, Y_R)$ shown FIGS. 1(*a*) and 1(*c*). When a single limb (i.e., hoof or foot) is on a plate 130, 120, the RFD system 100 calculates the position of that limb. When more than one limb is in contact with a floor plate 130, 120, the RFD system 100 calculates the position of an equivalent or resultant force, as discussed below.

A suitable load cell for this arrangement is Model RL35083 produced by Rice Lake Weighing Systems of Rice Lake, Wis. If a greater or lesser number of load cells 150 is desired, correspondingly and respectively decreasing or increasing the Ground Reaction Force (GRF) experienced by any individual load cell 150, alternative load cells may be selected to appropriately maintain the GRFs within the calibrated working ranges of each load cell. For applications involving cows, the inventors have determined that the GRFs are substantially vertical and GRF variations due to lameness, or the onset thereof, are determinable based on differences in these vertical GRFs. Therefore, bovine applications may employ a plurality of single-axis load cells measuring force in only the vertical direction, thus achieving a significant cost reduction over comparable multi-axis system.

However, the present invention also includes applications utilizing multi-axis load cells such as 2-axis, 3-axis, and n-axis load cells, where n is any integer, in any number and any combination. For example, a lesser number of multi-axis load cells 150 could be used in lieu of the four single-axis load cells of the embodiment described above for a bovine application. Alternatively, an equal number or greater number of such multi-axis load cells could be used, just as the number of single-axis load cells could be increased, as desired. Some embodiments of the present invention could, for example, advantageously utilize one or more load cells 150 per left or right plate 130, 120, wherein the load cell 150 is able to measure three orthogonal force components along the X, Y, and Z axes, as well as the moments about the axes, producing up to six outputs. These multi-axis load cells are particularly useful for measuring GRF components of hoof or foot movement in a plurality of axis, but may be also used to reduce the number of load cells required for an RFD, such as an RFD configured for a bovine application, by replacing the 4 single-axis load cells with two 3-axis load cells for each of the left and right plates 130, 120. Thus, in accord with the invention, the load cell 150 specifications and arrangements may be freely varied and optimized to identify ailments endemic to a particular animal type based on the physical manifestation of such ailment on the GRFs produced by the animal's hoof or foot against a load sensitive surface 130, 120.

In the above described aspect of the invention, the load cells 150 and left and right plates 130, 120 are mounted on a single base. As shown in FIG. 9, discussed in more detail below, the load cell 150 outputs are sampled by an A/D board 950, such as an Iotech DaqBook model 200, receiving signals from an external eight channel strain gage module 970, such as an Iotech DBK43A. These eight channels are read sequentially through a single channel amplifier 960 and the sampled data is stored in computer memory 906, 910 in a convenient computer readable medium, such as an ASCII file. The sampling rate of the A/D board is preferably set to 100 Hz, but may be increased in accord with frequency of the sampled events to provide an appropriate sampling rate, such as a sampling rate greater than the Nyquist rate, as known to those skilled in the art.

Following passage of the animal over the step-up 110 and over the left and right plates 130, 120, a ramp down 140 is disposed immediately after the left and right plates to permit egress of the animal from the RFD system 100. A suitable ramp down possesses a width of 127 cm and a length of 122 cm, although these dimensions may vary significantly in accord with space constraints, if any. Generally, the downgrade is maintained between about 5 to 15 to avoid injury to the animals. The ramp 140 preferably comprises the same layered structure as the left and right floor plates 130, 120. Alternatively, some animals, such as horses do not respond well to such ramps, steps, or height differences. Therefore, another embodiment of the invention advantageously incorporates the left and right floor plates 130, 120 into the floor itself so that the upper surface of the floor plates 130, 120 are substantially flush with the remainder of the floor surface.

A plurality of photocells, and corresponding reflective elements, may be disposed to measure each animals'speed through the RFD system 100. In one preferred aspect, illustrated in FIG. 1(c), three photocells 160 are sequentially arranged along the left or right plates 130, 120 so as to be triggered by the cow's brisket and rear flank as the cow passes though the line of sight of one of the three sequentially spaced photo-cells. Any number of photocells could be used in accord with the invention, however. Additionally, it is generally preferred that the photocells 160 be spaced along the entire length of the plates 130, 120, or may be grouped toward the center or toward one side in accord with the invention. Moreover, other devices commonly used to determine the speed of an object, such as but not limited to those using optics or light signals, such as laser pulse systems determining velocity using time-of-flight or phase shift techniques, or acoustically-based speed sensing devices may also be used.

The RFD system 100 is calibrated by placing a known or calibrated weight at predetermined (X, Y) positions along each of the left and right plates 130, 120 and recording the voltage produced by the individual load cells 150. In a preferred calibration technique, a calibrated load of 203.8 Kg is placed at (X, Y)=(18.74 cm, 99 cm).

Initial animal tests showed that a sound cow places her limbs at X values that range between 15 to 20 cm when passing through the RFD system 100. Accordingly, a longitudinal center line at X=18.74 cm was selected as a preferred calibration point, however, any point between 15 cm and 20 cm would suffice for this application. Correspondingly, the weight of the calibration weight and the location of the center line may be adjusted in accord with the size and weight of the group of animals to be observed. The system calibration points, shown as $C_L$ and $C_R$ in FIG. 1(c), are selected along the longitudinal center lines at $X_{L,R}$=18.74 cm. To calibrate the system, it is preferred that three calibrated weights be placed on each of the left and right plates 130, 120 at the designated calibration points to provide a known force in the negative Z direction and readings of each of the load cells 150 are measured and stored. In one aspect, the weights may be 113.2 kg, 158.6 kg, and 203.8 kg.

The reaction forces at each of the eight load cells 150 is evaluated, in one preferred aspect of the invention, via one or more finite element models (FEM), known to those skilled in the art, when the unit loads are applied at the left and right calibration points $C_L$ and $C_R$. Alternative calculation methods known to those skilled in the art may also be used to determine the reaction forces. Lines that pass through the zero load conditions and best fit, using conventional best fit techniques, to the three applied known loads establish the loading factors of the eight individual load cells 150. In other words, the calibration factors of the load cells 150 are calculated as a ratio of the computed applied loads to the individual load cell 150 readings. These factors, listed in Table 1 below, are stored computer 900 for later use by the calibration program. It is preferred that the calibration procedure be performed prior to use of the RFD; however, trending analyses may advantageously be performed to determine the degree of miscalibration over time for a particular application and environment to determine the efficacy of such per-use calibrations.

TABLE 1

Load distribution of the right and left floor plates as calculated by the finite element model and corresponding calibration factors of the system eight load cells.

| Load Cell | Load Distribution Obtained by FEM | Calibration Factors Kg/Volt |
| --- | --- | --- |
| LC1 | 0.08 | 0.0257 |
| LC2 | 0.06 | 0.0111 |
| LC3 | 0.44 | 0.0324 |
| LC4 | 0.42 | 0.0273 |
| LC5 | 0.44 | 0.0264 |
| LC6 | 0.43 | 0.0260 |
| LC7 | 0.07 | 0.0229 |
| LC8 | 0.06 | 0.0286 |

Figure 3:
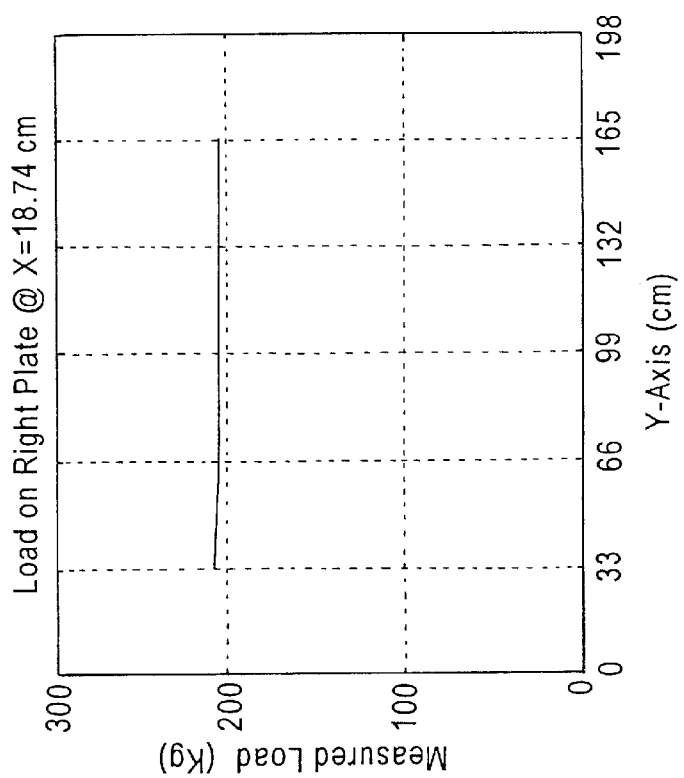
FIGS. 3(i)–3(iv) are charts showing the accuracy of body weight measurements, wherein FIGS. 3(i) and 3(ii) illustrate weight readings of the left and right plate when a weight of 203.8 Kg is placed at five points along the line X=18.4 cm and the percentage errors of these measurements for the left and right plates in FIGS. 3(iii) and 3(iv), respectively.
Figure 3I:
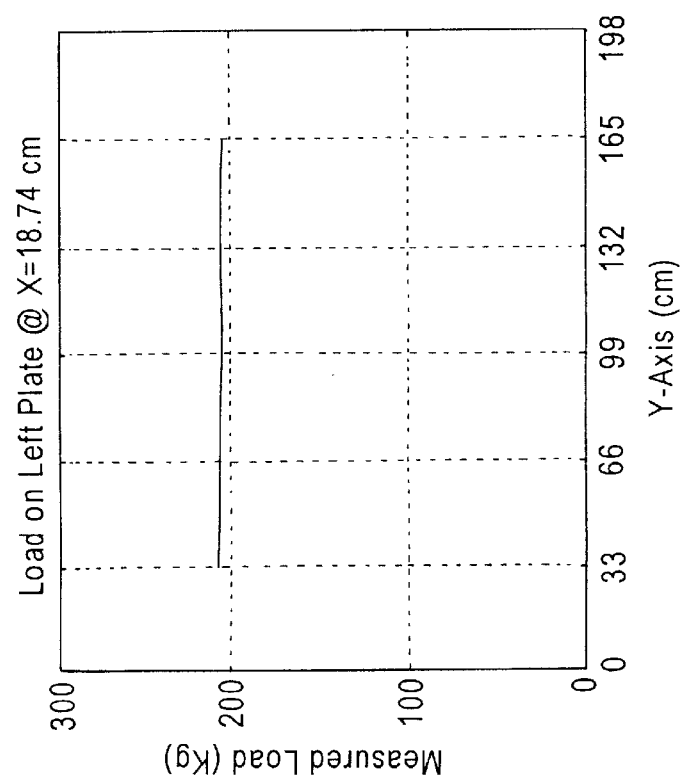
Figure 3:
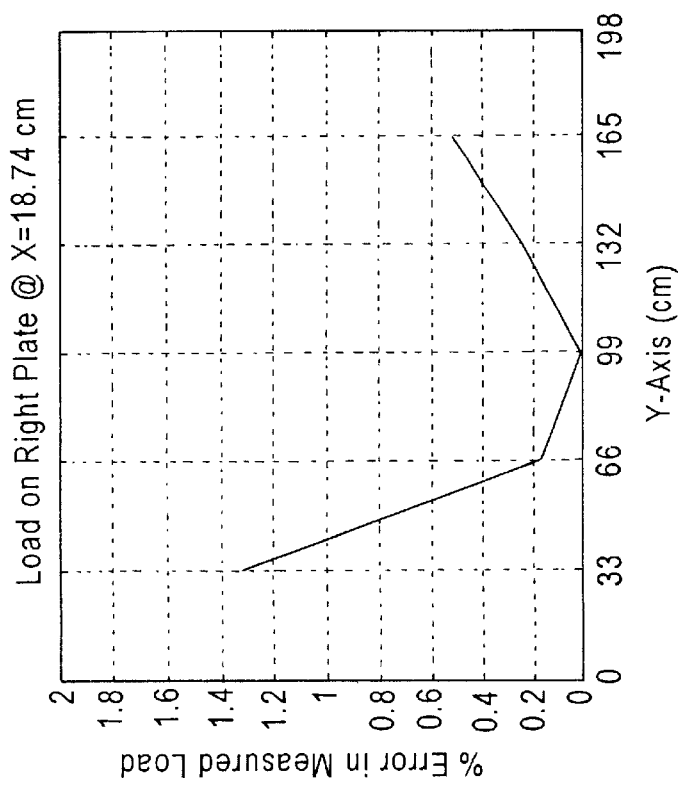
Figure 4:
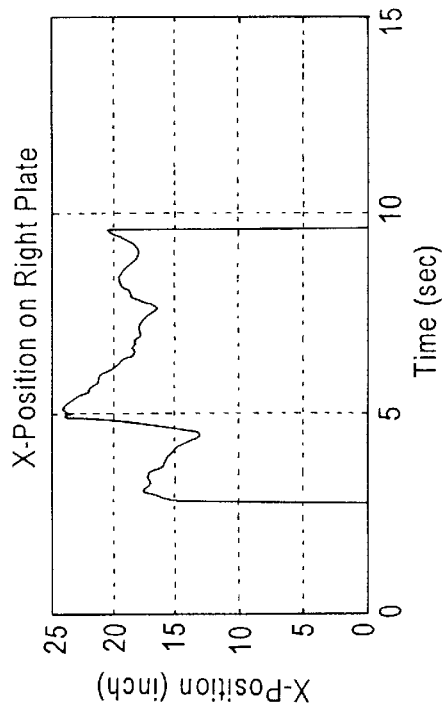
FIGS. 4(i)–4(vi) are graphs illustrating a typical time history of X (FIGS. 4(i) and 4(ii)) and Y (FIGS. 4(iii) and 4(iv)) coordinates of the cow's limb positions when passing through the RFD unit. Corresponding ground reaction forces are depicted in FIGS. 4(v) and 4(vi).
Figure 4:
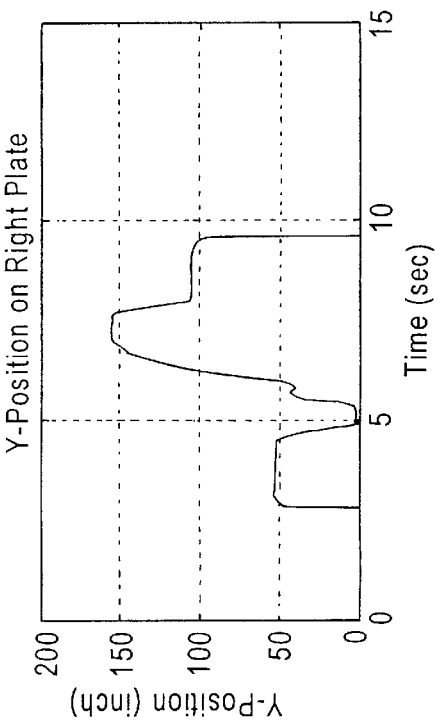
Figure 4I:
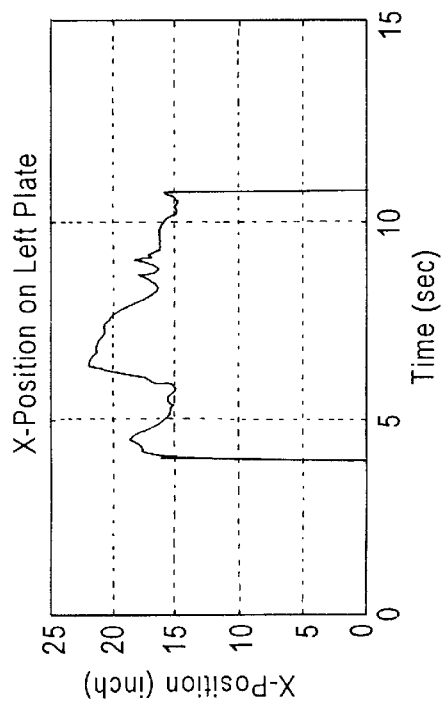
Figure 4:
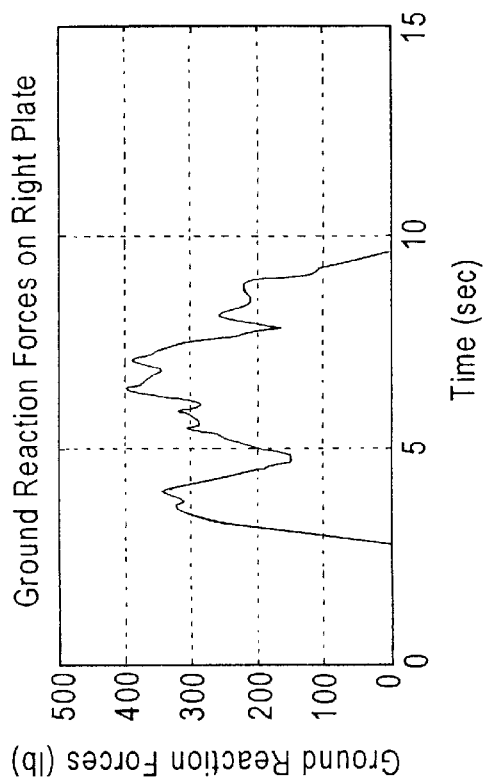
Figure 4V:
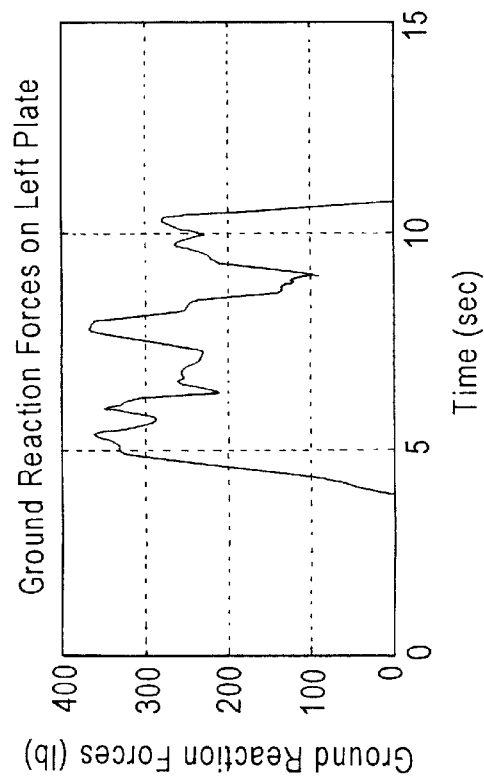
Figure 5:
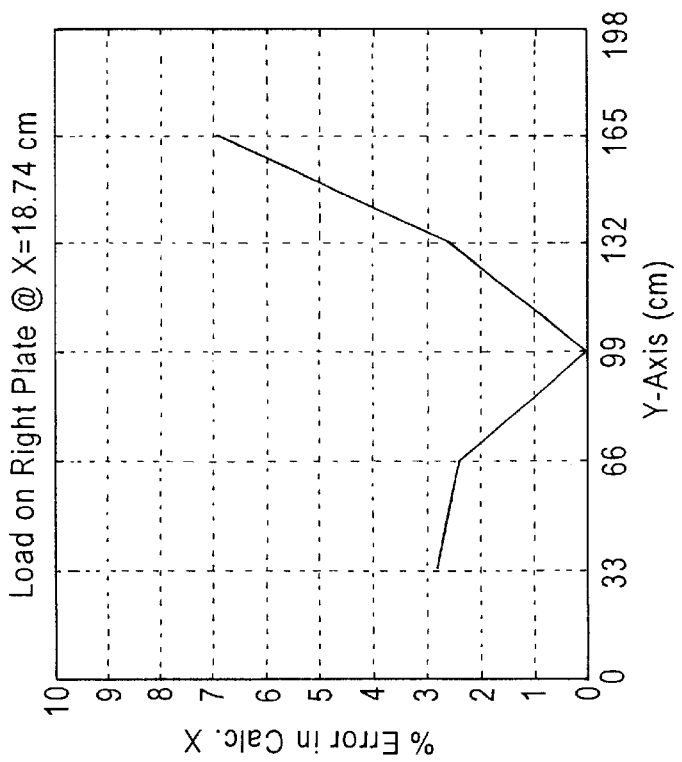
FIGS. 5(i)–5(iv) are graphs showing the accuracy of the X and Y coordinates of the limb positions.
Figure 5I:
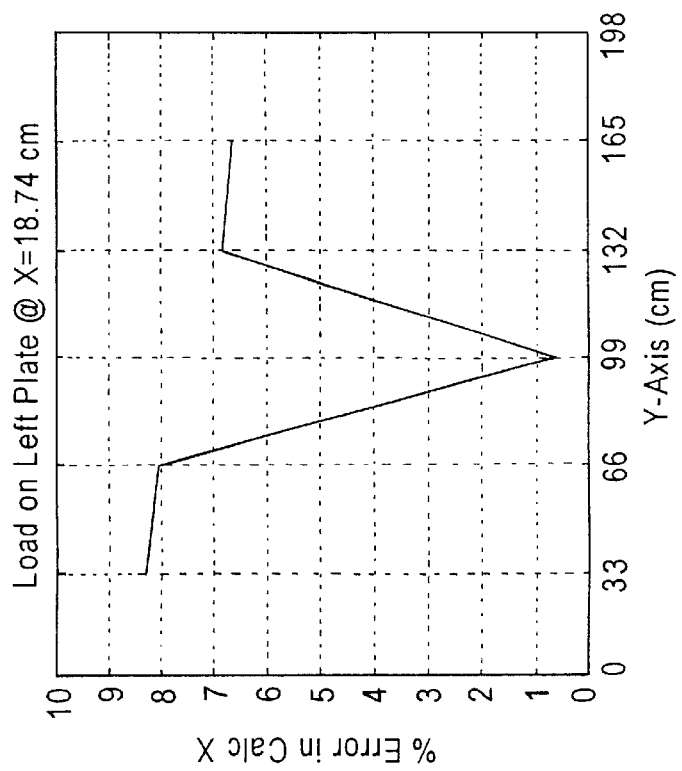

To characterize the accuracy of the measurements of the ground reaction forces and total body weight measurements, a weight of 203.8 kg is placed at five points along the lines $X_{L,R}$=18.74 cm. Each measured load and its location is measured and calculated, respectively, in a manner discussed below. Errors of the load measurements on the right and left plates have been found to be less than 1.3% and 1.7%, respectively, as shown in FIGS. 3(iv) and 3(iii), respectively. The resulting error locations along the X and Y axes in the right plate 120 were found to be less than 1.3 and 3.1 cm, respectively, and the corresponding errors in the left plate 130 are less than 1.5 and 2.4 cm, respectively.

Figure 2:
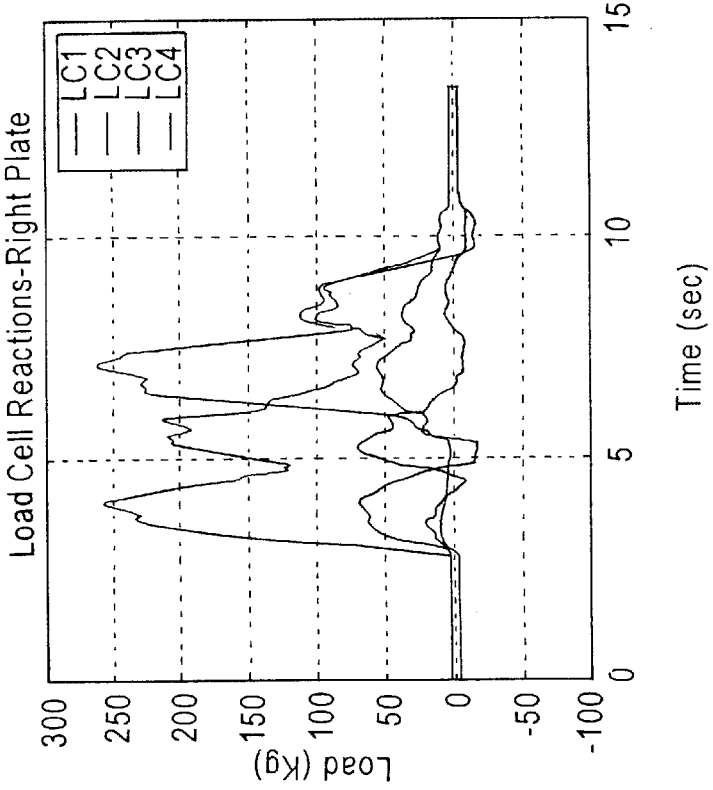
FIGS. 2(i)–2(iv) are graphs depicting the load cell reactions of the left and right plates plotted as a function of time ((i) and (ii)), the animal's walkthrough speed as measured by a photo cell array (iii), and the animal's body weight calculated by summing the load cell reactions (iv).
Figure 2I:
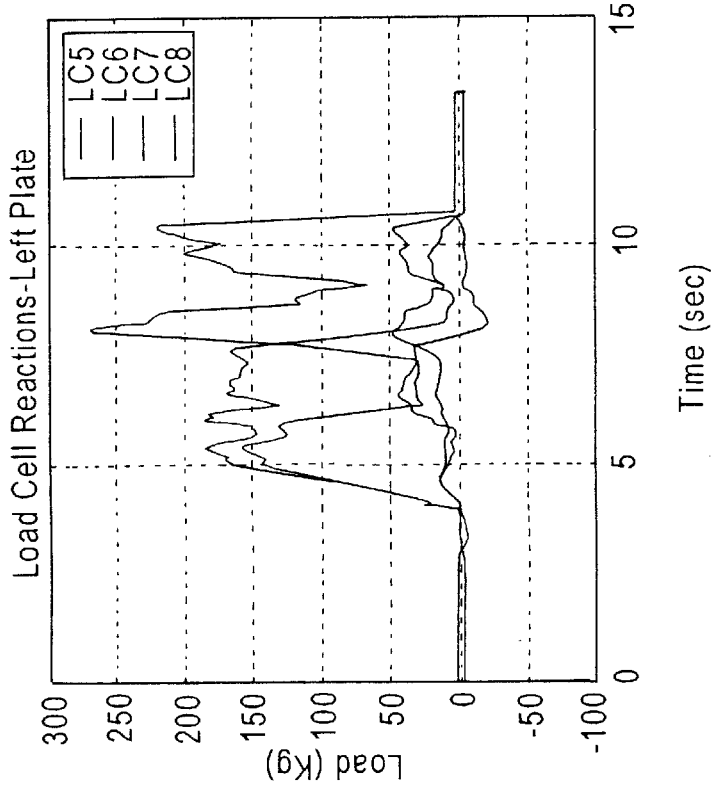

In the RFD system 100, load cell 150 reactions to the cow's passage are recorded as a function of time (see FIGS. 2(i) and 2(ii)) while the aforementioned array of photocells 160 measures the walkthrough speed (FIG. 2(iii)). Summation of load cell 150 reactions provides an accurate measurement of the cow's body weight. As shown in FIG. 2(iv), for example, the body weight of cow 18 is determined to be 672.7 Kg.

Turning to the calculations executed by the computer 900 in the analysis of the animal's walking gait and weight, the load cell 150 reactions are used to calculate the X and Y coordinates of the cow's limb positions and the associated left and right Ground Reaction Forces (GRF), previously mentioned. In these calculations, it is assumed that the right and left legs of the cow make contact with the corresponding right and left plates 130, 120 without crossover, and that a single limb is in contact with each of the right and left plates. However, when two legs are detected on a plate 130, 120, the position of an equivalent reaction force is calculated. This equivalent force is analogous to the center of gravity of the left and right sides of the animal. The Reaction Force of each of the four load cells 150 associated with the left plate 130, designated as "$R_{Lci}$", or the Reaction Force of each of the four load cells 150 associated with the right plate 120, designated as "$R_{Rci}$", are added together to calculated the GRF for that side. These individual reaction forces and the GRF for each side are used to calculate the limb contact positions with respect to the X and Y-axes.

The X and Y limb contact positions are calculated by summing the moments in the X-axis and Y-axis directions. Specifically, the $GRF_R$ and $X_R$ and $Y_R$ contact limb positions of the right plate are calculated as:

$$GRF_R = \sum_{i=1}^{4} R_{Lci} \quad (1)$$

$$X_R = \frac{\sum_{i=1}^{4} [X_{Lci} \cdot R_{Lci}]}{\sum_{i=1}^{4} R_{Lci}} \quad (2)$$

$$y_R = \frac{\sum_{i=1}^{4} [y_{Lci} \cdot R_{Lci}]}{\sum_{i=1}^{4} R_{Lci}} \quad (3)$$

where $R_{Lci}$ is the reaction force read by the i-th load cell, and $X_{Lci}$ and $Y_{Lci}$ are the X and Y coordinates of the load cells positions, as depicted in FIG. 3. The corresponding GRF and limb positions of the left plate are calculated in a similar way:

$$GRF_L = \sum_{i=5}^{8} R_{Lci} \quad (4)$$

$$x_L = \frac{\sum_{i=5}^{8} [X_{Lci} \cdot R_{Lci}]}{\sum_{i=1}^{8} R_{Lci}} \quad (5)$$

$$y_L = \frac{\sum_{i=5}^{8} [y_{Lci} \cdot R_{Lci}]}{\sum_{i=5}^{8} R_{Lci}} \quad (6)$$

The time history of the X and Y limb positions and the left and right GRF values for a sound cow that has passed through the device are depicted in FIG. 3. The X and Y limb positions and the GRF values, shown in FIG. 3, are used to calculate various limb movement variables, as discussed in greater detail below. These limb movement variables are analyzed to objectively determine whether an animal, such as a cow, has hoof, foot, or leg ailments. Analysis of these limb movement variables are the key to identifying lame animals and detecting which limb of an animal is afflicted with an ailment well before the ailment is manifested in a manner detectable by purely visual observation of the animal's movement. The limb movement variables are calculated by analyzing the X, Y and GRF values and the walking speed of each animal passing through the RFD system 100.

Figure 6:
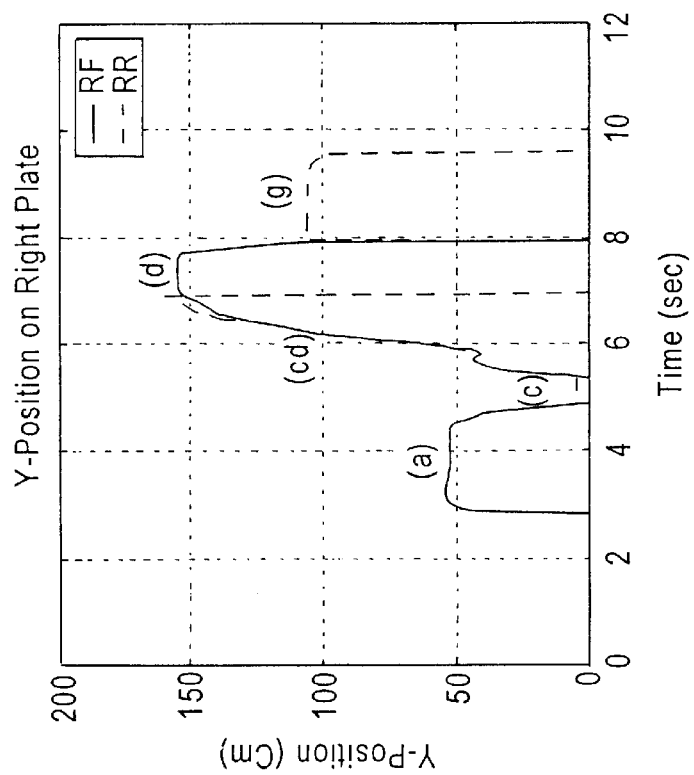
FIGS. 6(i)–6(iv) are graphs showing the time history of the Y coordinate of a sound cow's limb positions on the left and right plates (FIGS. 6(i) and 6(ii), respectively) and the corresponding normalized ground reaction forces (GRF) (FIGS. 6(iii) and 6(iv), respectively) obtained by dividing the GRF by the animal's body weight.
Figure 6I:
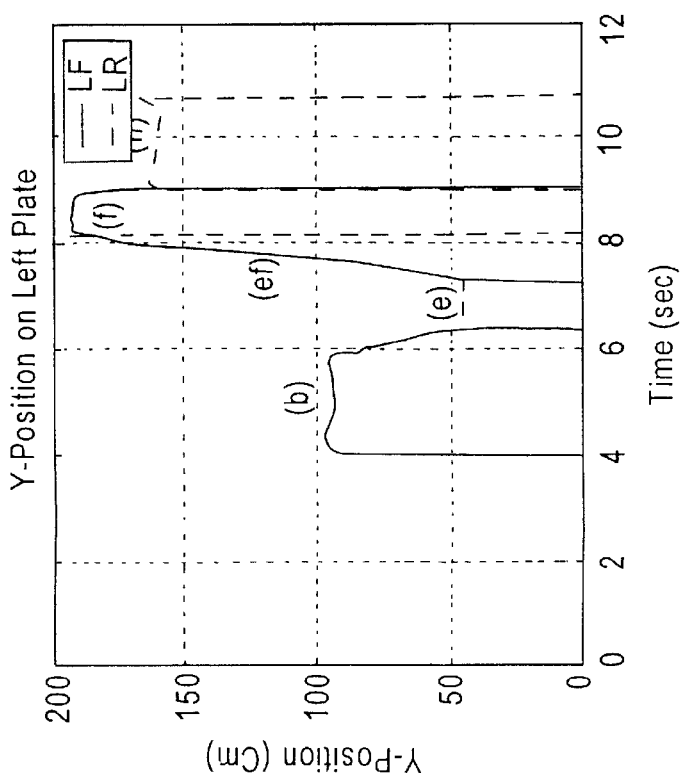
Figure 6:
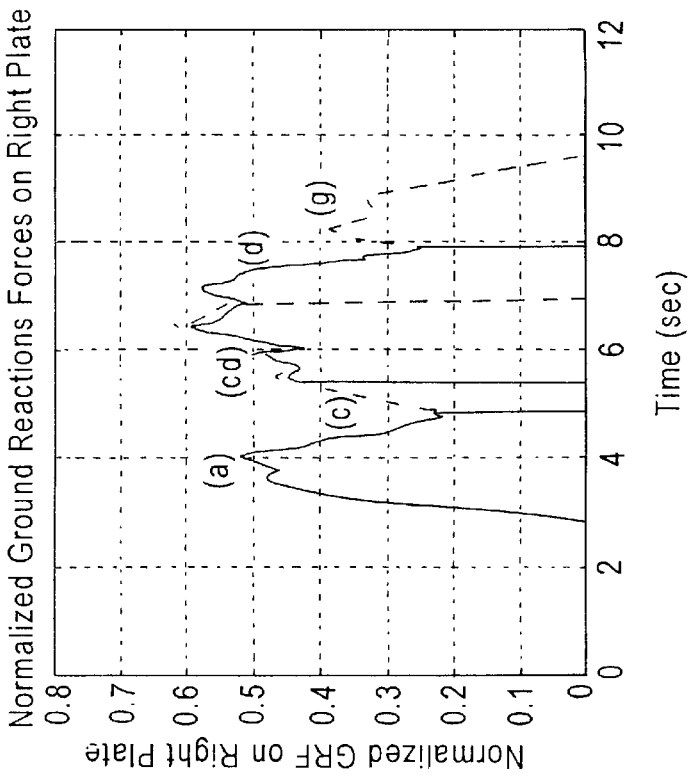

Various limb movement characteristics are calculated from the information depicted in FIG. 6. Table 2 below lists the values of non-limiting limb movement variables:

(i) normalized peak ground reaction force PRGF, (ii) impulse which is the integral of the normalized GRF with respect to time, (iii) stance time, the time during which a limb is in contact with the floor plate, (iv) normalized average ground reaction force AGRF which is the impulse divided by the stance time, (v) step size of individual limbs, (vi) speed of animal movement when a particular limb contacts the floor, (vii) the product of the impulse and cow speed which results in a characteristic unit length;

(viii) the "m-energy", defined herein as the integral of the magnitude of the GRFs with respect to the frequency in the frequency response domain;

(ix) the "p-energy", defined herein as the integral, over the frequency domain, of the product of the magnitude of the GRFs and frequency; and (x) understep of the animal, for a left side or right side of the animal, such as a horse, defined as the Y position of the fore limb placement ($Y_{FORE}$) minus the Y position of the hind limb placement ($Y_{HIND}$), wherein a positive value indicates that that the animal puts the front limb ahead of the rear limb as it moves through the RFD and wherein a negative value indicates that the animal puts the rear limb ahead of the front limb as it moves through the RFD.

Figure 7I:
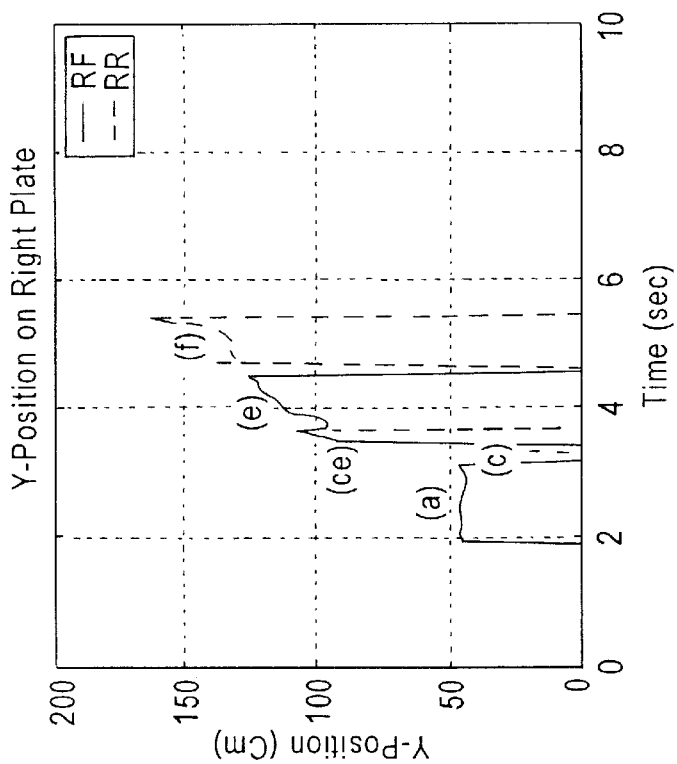
FIGS. 7(i)–7(iv) are graphs showing the time history of the Y coordinate of a lame cow's limb positions on the left and right plates (FIGS. 7(i) and 7(ii), respectively) and the corresponding normalized ground reaction forces (FIGS. 7(iii) and 7(iv), respectively).
Figure 7:
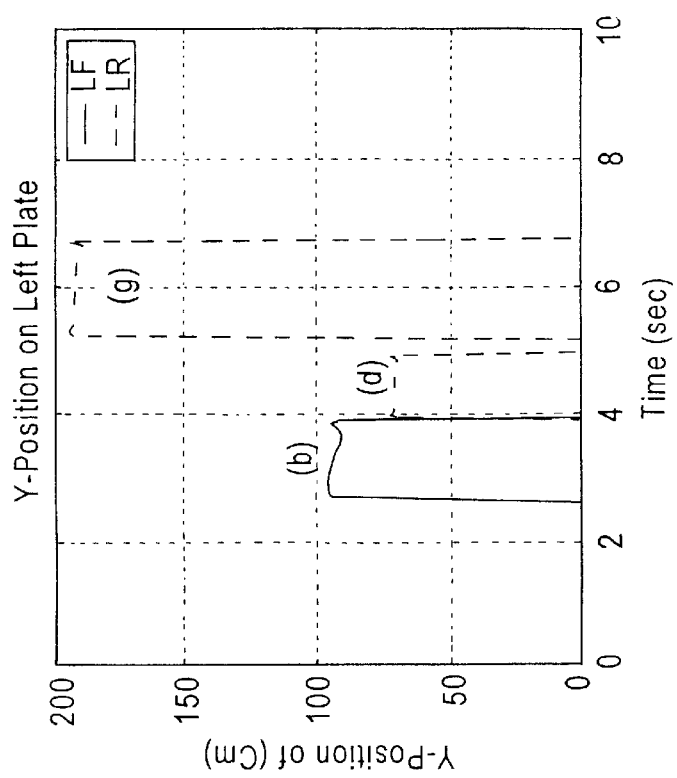
Figure 7:
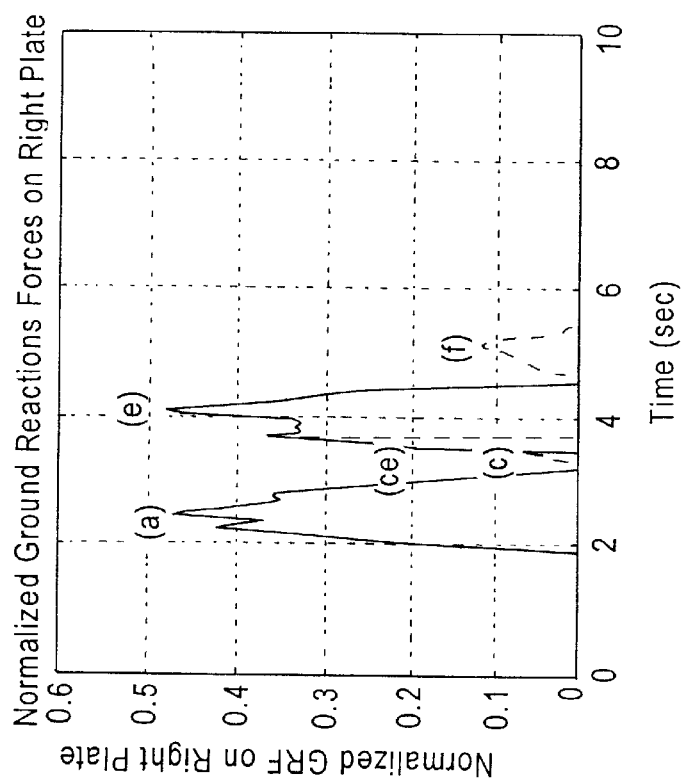

Examples of the usefulness of these limb movement variables are illustrate in FIGS. 6 and 7. A full set of leg positions, X and Y values, and ground reaction forces, GRF values are plotted in FIG. 6 for a healthy cow and in FIG. 7 for a lame cow. The identification of the time, position, and intensity of individual front and rear limb contact with the left and right plates 130, 120 is premised, in part, on the fact that the left and right forelimbs strike the plate first and the hind limbs follow behind. Using this premise, the sequence by which the animal's limbs contacted the plates 130, 120 may be determined. Photocell 160 data is used to confirm the position of the cow and to verify that only one cow is on the force plates 130, 120. Limb movement variables, provided below, may be calculated when a single leg is in contact with the left or right plate or even when two limbs are in contact with a single plate. The typical RFD output consists of both single and two limb positions.

The stance time may be computer for a fore limb, a rear limb, or for both a fore and rear limb, or for all limbs. The total time that a limb is in contact with the left or right plate 130, 120 may be calculated by taking a difference between a first time at which an applied force from the selected limb first exceeds a predetermined threshold force as the limb is applied to the plate and a second time at which the applied force from the limb falls below the predetermined threshold force. This defines a discrete force application event for the selected limb. In one aspect, the predetermined threshold is simply a force that is used as a trigger to start and stop the computation of the stance time. The preselected force is generally between 0.00 to about 5.0 lbf, but could be 10.0 lbf, 20.0 lbf, or higher, so long as a consistent value is used.

When only one limb is in contact with the plate 130, 120, the position of that leg is calculated by the computer 900 utilizing equations (1) through (6), above, and output to an appropriate output device, such as display 912 or attached printer, or to a remote device through communication interface 918. For example, FIG. 6 shows a sound cow that has placed her right forelimb first at Y=53 cm (FIG. 6(*ii*)(*a*)) and then her left forelimb at Y=96 cm (FIG. 6(*i*)(*b*)). Next, the right hind limb is placed at Y=8 cm (FIG. 6(*ii*)(*c*)) and the right forelimb was moved to Y=155 cm (FIG. 6(*ii*)(*d*)).

Concurrent placement of both the right fore and hind limbs on the right plate 120 is represented in FIGS. 6(*ii*) and 6(*iv*) as "cd". Similarly, the left hind and fore limbs are then placed at Y=46 cm and Y=193 cm, respectively, as shown in FIGS. 6(*i*) and 6(*iii*). Concurrent placement of both the left fore and hind limbs on the left plate 130 is represented as "ef". At the end of the cow's walk-through, the right and left hind limbs were placed at Y=107 cm (FIG. 6(*ii*)(*g*)) and Y=163 cm (FIG. 6(*i*)(*h*)), respectively.

Normalized GRF values of the sound cow's left and right limbs are depicted in FIGS. 6(*iii*) and 6(*iv*), which illustrate that the peak GRF values of the right and left fore limbs are 0.55 (see FIG. 6(*iv*)(*a*)) and 0.54 (see FIG. 6(*iii*)(*a*)), respectively, whereas the peaks of the right and left hind limbs are 0.39 (see FIG. 6(*iv*)(*g*)) and 0.41 (see FIG. 6(*iii*)(*h*)), respectively.

The numerical values selected limb movement variables of sound cow 18 are listed in Table 2, below.

TABLE 2

Limb movement variables of sound cow 18.

| Cow | Limb Movement Variables | Individual Limbs | | | |
| --- | --- | --- | --- | --- | --- |
| | | Left Front [LF] | Right Front [RF] | Left Rear [LR] | Right Rear [RR] |
| Sound 18 | Normalized PGRF | 0.54 | 0.55 | 0.41 | 0.39 |
| | Stance time (sec) | 2.30 | 1.95 | 1.70 | 1.65 |
| | Impulse (sec) | 0.88 | 0.71 | 0.52 | 0.45 |
| | Normalized AGRF | 0.38 | 0.37 | 0.31 | 0.27 |
| | Step size (cm) | 99 | 101 | 115 | 101 |
| | Speed of animal (cm/sec) | 43 | 43 | 43 | 46 |
| | Impulse * Speed (cm) | 38 | 31 | 23 | 21 |

Similarly, FIG. 7 depicts the Y coordinate and normalized GRF of a cow (lame cow 94) that is known to be lame as a result of sole bruising in her right rear limb. As shown by FIG. 7, the lame cow first places her right front limb at Y=46 cm (FIG. 7(*ii*)(*a*)) and left front limb at Y=97 cm (FIG. 7(*i*)(*a*)). Subsequently the right and left rear limbs are placed at Y=30 cm (FIG. 7(*ii*)(*c*)) and Y=64 cm (FIG. 7(*i*)(*d*)), respectively. Then, the right front limb is placed at Y=114 cm (FIG. 7(*ii*)(*e*)) and the right plate 120 experiences two limb contact, designated as "ce" in FIG. 7(*ii*). Finally, the left and right rear limbs were placed at Y=198 cm (FIG. 7(*i*)(*g*)) and Y=127 cm (FIG. 7(*ii*)(*f*)), respectively. The varying Y position reading (of 127 to 165 cm) when the right hind limb contacts the floor 120 illustrates a shift in the cow's weight placement toward the toe and off the heel.

Normalized GRF values of the lame cow's left and right limbs are depicted in FIGS. 7(*iii*) and 7(*iv*), which illustrate that the peak GRF values of the right and left fore limbs are 0.47 (see FIG. 7(*iv*)(*a*)) and 0.53 (see FIG. 7(*iii*)(*a*)), respectively, whereas the peaks of the right and left hind limbs are 0.12 (see FIG. 7(*iv*)(*g*)) and 0.50 (see FIG. 7(*iii*)(*h*)), respectively. Thus, the lame right hind limb produces a noticeably low peak GRF value.

The numerical values selected limb movement variables of lame cow 94 are listed in Table 3, below.

TABLE 3

Limb movement variables of lame cow 94.

| Cow | Limb Movement Variables | Individual Limbs | | | |
| --- | --- | --- | --- | --- | --- |
| | | Left Front [LF] | Right Front [RF] | Left Rear [LR] | Right Rear [RR] |
| Lame 94 | Normalized PGRF | 0.53 | 0.47 | 0.50 | 0.12 |
| | Stance time (sec) | 1.20 | 1.20 | 1.45 | 0.75 |
| | Impulse (sec) | 0.39 | 0.39 | 0.51 | 0.05 |
| | Normalized AGRF | 0.33 | 0.32 | 0.35 | 0.07 |
| | Step size (cm) | NA | 72 | 121 | 110 |
| | Speed of animal (cm/sec) | 97 | 89 | 56 | 56 |
| | Impulse * Speed (cm) | 38 | 35 | 29 | 3 |

Note the low values of normalized PGRF, impulse, AGRF, and the product of impulse and speed associated with the right rear limb of cow 94. Similar results were obtained in additional tests conducted on groups of sound cows and lame cows, as evident in the tables of test data presented in FIGS. 11 and 12.

When both the fore and rear limbs contact the plate, the RFD captures the position of the equivalent (resultant) applied load. These two limb positions and the corresponding equivalent loads are shown, for example, in FIGS. 8(*a*), (*b*), (*c*), (*d*). This equivalent load can be decomposed into the loads of the individual limbs as explained below.

From the time history of the Y position before and after the two limb contact one skilled in the art can recognize the positions of the front (Y2) and rear limbs (Y1). In FIG. 9(*a*), for example, the left rear limb is placed at Y1=49 cm and the left front limb is placed at Y2=190 cm. At the point in time between approximately 7.5 seconds and 8.5 seconds, both the front limb and the rear limb are in contact with the left plate 130. Assuming no slip conditions in accord with the anti-slip component of the above-described aspects of the force plate 130, the value of Y1 and Y2 do not change and are known. Following a determination that two limbs are in contact with a force plate, such as the example shown in FIG. 8(*a*), the GRF of the individual limbs may be calculated by solving the following two limb model presenting two equations with two unknowns:

$$F1+F2=\Sigma[R_{LCi}] \quad (7)$$

$$F1*Y1+F2*Y2=\Sigma[Y_{LCi}*R_{LCi}] \quad (8)$$

Figure 8E:
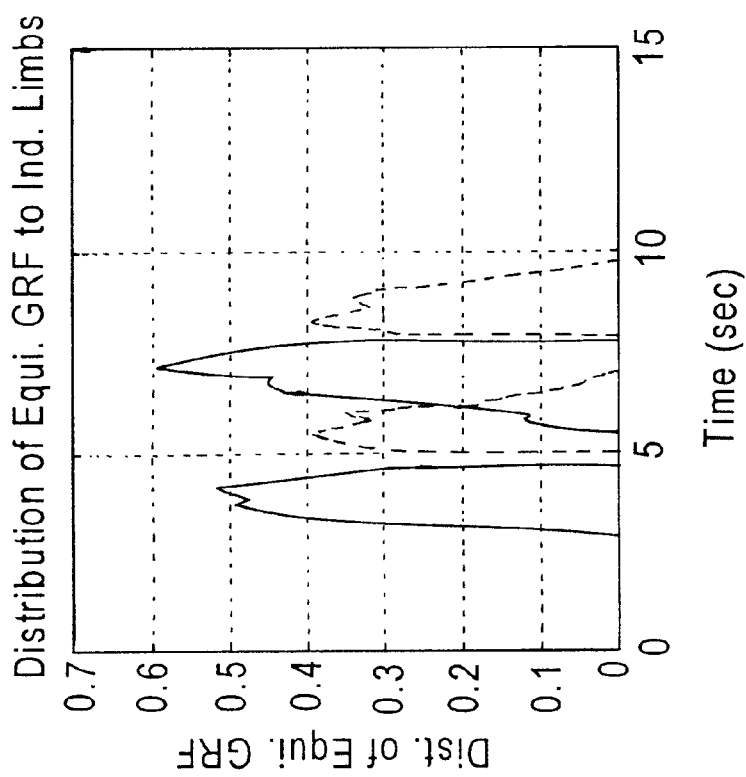
Figure 8F:
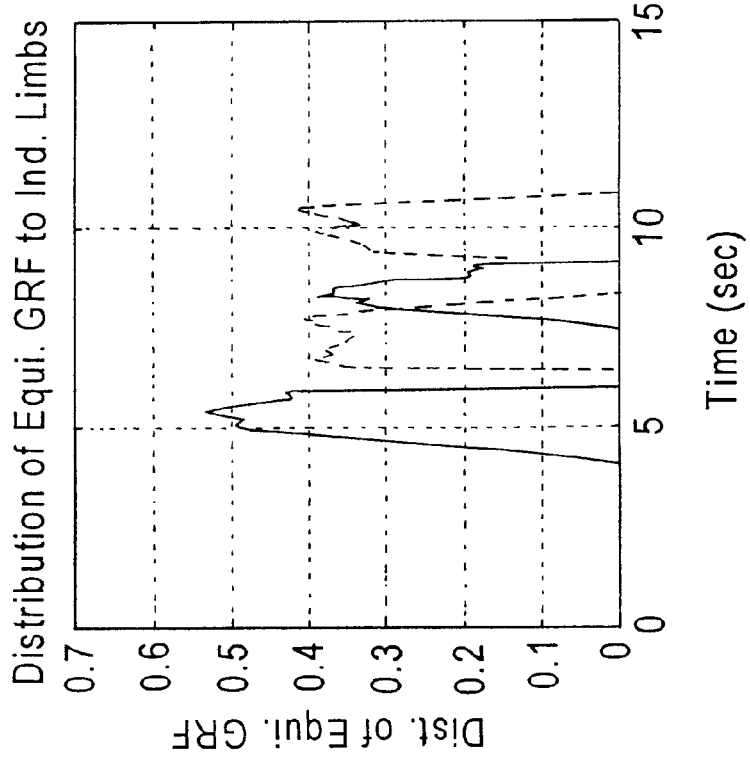

Where, i=1 to 4 for left and right plate load cells, $R_{LCi}$=load cell outputs, $Y_{LCi}$=load cell Y positions, F1=GRF of the rear limb and F2=GRF of the front limb. By solving these two limb model equations, the GRF of the individual limbs may be obtained as shown in FIG. 8(*e*) and 8(*f*).

Furthermore, the limb movement variables can be used to evaluate the symmetry characteristics of the animal movement (e.g., walking, trotting, running, etc.) parameters. A symmetry factor ("SF") is expressed as:

$$SF = \frac{R_{LMV} - L_{LMV}}{R_{LMV} + L_{LMV}} \quad (9)$$

where $R_{LMV}$ and $L_{LMV}$ correspond to right and left limb movement variables. A zero SF value represents a symmetric condition whereas positive and negative values represent dominance of the right and left sides, respectively. In the extreme case where a limb movement variable approaches a zero value, SF converges to 1.0 when the left limb is lame, and −1.0 when the right limb is lame. Hence, SF is an intensity indicator of lameness that utilizes the bilateral symmetry of the animal's body to examine the extent to which a selected left or right limb movement variable differs from the corresponding value of its counter side. Table 4 lists the SF values of the limb movement variables of the sound cow of FIG. 6 and the lame cow of FIG. 7.

TABLE 4

The SF values of the limb movement variables of cows 18 and 94.

| Limb | Cow 18 - Sound | | Cow 94 - Lame | |
| --- | --- | --- | --- | --- |
| Movement Variables | Symmetry of Front limbs | Symmetry of Rear limbs | Symmetry of Front limbs | Symmetry of Rear limbs |
| Normalized PGRF | 0.01 | −0.03 | −0.06 | −0.61 |
| Stance time | −0.08 | −0.02 | 0.00 | −0.32 |
| Impulse | −0.11 | −0.07 | 0.00 | −0.82 |
| Normalized AGRF | −0.01 | −0.07 | −0.02 | −0.60 |
| Step size | 0.01 | −0.07 | NA | −0.05 |
| Speed of animal | 0.00 | 0.03 | −0.04 | 0.00 |
| Impulse*Speed | −0.10 | −0.05 | −0.04 | −0.81 |

Note the low SF values (less than 0.111) of the sound cow 18, and the high values (as high as 0.82) of the lame cow 94. These measurements are indicative of still further diagnostic benefits afforded by the method and apparatus of the present invention by indentification and analysis of precursors to lameness, such as but not limited to various SF indicators, PGRF, Impulse, AGRF, and Impulse*Speed. Present test data does not seem to indicate that step size and speed are significantly affected by early stages of lameness. However, such correlation has not conclusively been ruled out and may be determinable upon a sufficient sample population in accord with the present invention.

Figure 9A:
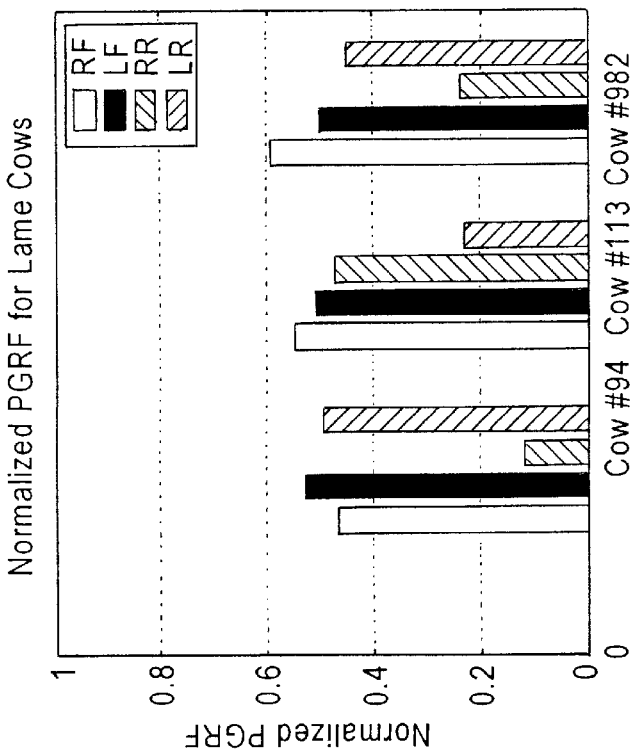
FIGS. 9(a)–9(d) are bar charts showing normalized peak ground reaction force (PGRF) for sound cows and for lame cows (FIGS. 9(a) and 9(b), respectively) and Symmetry Factors of sound cows and lame cows.
Figure 9C:
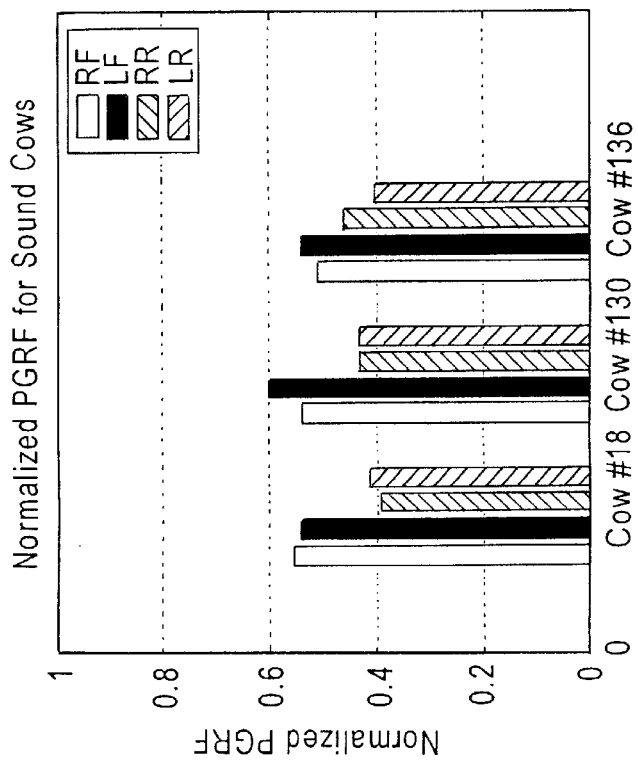
Figure 9D:
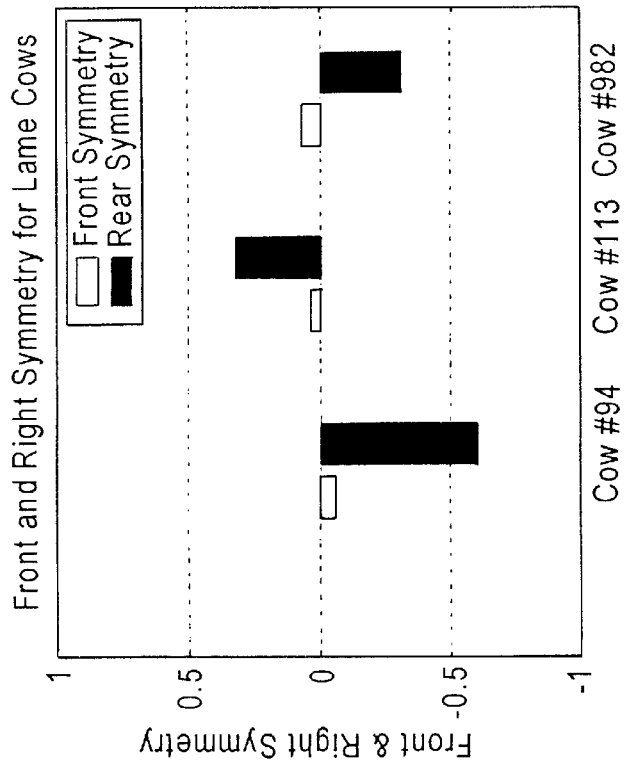
Figure 9B:
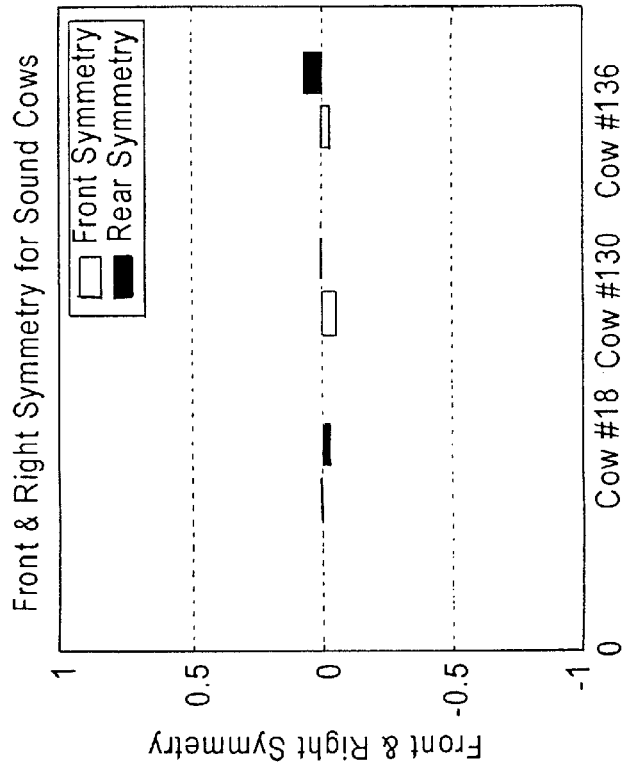

The RFD system 100 was further tested on three sound cows and three lame cows. FIG. 9 depicts the test results as normalized PGRF and symmetry factor bar charts. FIG. 9(i) depicts the normalized PGRF values of sound cows (cows 18, 130, and 136), wherein the typical values of 0.5 for the front limbs and 0.4 for the rear. The corresponding PGRF values for the three lame cows (cows 94, 113, and 982), shown in FIG. 9(ii), are 0.12 (right rear limb), 0.24 (left rear limb), and 0.25 (right rear limb). FIG. 9(iii) and 9(iv) further depict the symmetry factors of the front and rear limbs. In accord with other test results, the SF values for the sound cows 18, 130, and 136, are better than 0.07, whereas the SF values of cows 94, 113, and 982 are −0.61, 0.33, and −0.30, respectively.

As noted previously, various conventional lameness detection schemes employ visual observations of the animal's posture or gait to obtain relatively assign a value corresponding to the severity of the lameness. In an effort to objectively characterize the status or severity of hoof and leg ailments (e.g., lameness), the present invention advantageously determines various limb movement characteristics through the RFD system. The RFD system can be used to measure multiple variables representative of limb movements, such as: (a) peak value of ground reaction force (GRF) of individual limbs, (a) integral of GRF with respect to time, (c) stance time, (d) average GRF, (e) step size, (f) integral of the Fourier transformation of the GRF signature with respect to frequency, and (g) the integral with respect to frequency of the Fourier transform of the GRF signature multiplied by the frequency, (h) various symmetry variables, and numerous other combinations, derivatives, and integrals. To allow comparisons among different cows, the variables representative of limb movements may be normalized with respect to body weight and symmetry variables may be used to compare left to right limbs for the same speed of body movement.

Additionally, just as the limb movement variables can be used to evaluate the symmetry characteristics of the animal walking parameters, for example, the limb movement variables may be advantageously used to actually relate clinical lameness diagnoses of individual limbs to the measured values of limb movement variables. As previously noted, the conventional techniques utilize subjective and non-quantitative visual observation. In accord with the inventive method, a statistically sufficient sample population of a selected animal, such as a dairy cow or horse, for example, is evaluated using the RFD to obtain limb movement variables for each animal. Subsequent to or preceding the RFD testing on the sample population, a determination is made by a veterinarian or other person trained to diagnose lameness, or other ailment or condition manifesting in the animal's movement.

With this knowledge of the actual physical condition of each animal, correlations may be drawn between individual limb variables or combinations of limb variables such as but not limited to any data manipulation, such as but not limited to products, sums, differences, dividends, derivatives, integrals, log charts, etc., conventionally used to relate data to definable patterns used to then generate a function to describe an observed phenomena such that a function of one or more variables may be established between the limb movement data, limb movement variables, and/or combinations thereof, and lameness, for example. Moreover, it is within the scope of the invention to perform one or more additional RFD tests (e.g., a "subsequent" test) immediately or soon after completion of a successful first test. This subsequent test may be used to validate or confirm the results of the first test, particularly when the first test indicates the onset of a potential problem with the animal.

In this manner, the invention is not limited to simple determinations of "sound" or "lame", but is capable of measuring and defining many levels or degrees of lameness, which facilitates early detection of potential lameness precursors and thereby promotes animal well-being. In accord with the invention, inventors have performed logistic regression and discriminant analyses, such as by LOGISTIC™, STEPDISC™, and SAS™ computer program subroutines, known to those skilled in the statistical analysis art, to determine a strong correlation between the visual lameness scoring scale and the GRFs determined by the apparatus of the invention. Specifically, the correlation between the visual lameness scoring scale and the GRFs can be captured by the average GRF values ($p<0.05$), or in other words, a 95% confidence level, of individual limbs. The model or formulas generatable therefrom, such as but not limited to an estimated lameness index derived as the weighted sum of these probabilities, predict probabilities that a cow is sound, mildly lame, and lame. Further, it is to be appreciated that the models or formulas generated from the data obtained by the RFD system may include many degrees of lameness, or other observed characteristic, in accord with a statistically significant sample size. For example, 5 degrees of lameness, or even 10 or more degrees of lameness may be gleaned from sufficient data samples. The inventors have determined, with respect to a small sample size of 16 mildly lame and sound dairy cows, that the diagnostic results of the visual scoring scale and the new estimated lameness index matched perfectly for lame cows and the visual scores and lameness index of 2 out of 16 mildly lame and sound cases exhibited discrepancies. Thus, above example provides one instance wherein the limb movement data, limb movement variables, and mathematically manipulated combinations or variations thereof can be used to develop objective measures of dairy cow lameness in combination with existing clinical lameness diagnoses of individual limbs. However, it is to be understood that the limb movement data, limb movement variables, and mathematically manipulated combinations or variations thereof can be used to develop many other objective measures of dairy cow lameness or other characteristics of interest in combination with existing clinical lameness diagnoses of individual limbs and these objective measures could include many levels of severity or interest.

In one aspect of the invention, therefore, models for an ailment, such as lameness, as varying degrees of severity thereof, may be developed for specific animal-types based on the data obtained by the RFD. Such models could thus determine the lameness score of individual limbs based on the values of a set of important limb movement variables and could account for many environmental variables such as geographic location, climate, living conditions, and even farm management styles.

In still another aspect of the invention, following development of correlations between the raw data and/or derived data, as noted above, obtained from the RFD system, the RFD system can be largely or entirely automized. For example, an RFD system could be placed in a tract that the animals pass through with a frequency commensurate with at least a desired diagnostic frequency and the system may be set up and calibrated in advance. As previously noted, trending data of the RFD system calibration may be used to determine whether or not a particular application or environment of the RFD system would permit re-calibrations at a frequency less than the diagnostic test frequency. In such automatic operation, if the computer determines, based on the raw and/or derived data, that a potential malady is present in the animal, the computer could output a signal to identify the animal in the RFD system as a suspect animal. Owing to automatic operation, one aspect of the invention includes a means for identification or labeling of the animal for subsequent follow-up by veterinarian. For example, one or more dye markers, ink jets, or other marking device, may provided at the exit of the RFD to place a temporary mark on an animal as it exits the RFD system. These dye markers, or other marking devices, may place a temporary colored mark on the animal's hide to designate the occurrence of an ailment. Various colors could also be used as an indicator of severity. Alternatively, an imaging system could be used to image the animal or a part thereof, such as a conventional location of a brand or marking or ear tag and store the information on the computer memory or transmit the information to a remote location.

Still further, the animals may be equipped with electronic memory devices or data tags, such as but not limited to those manufactured by SanDisk Corp. of Sunnyvale, Calif. Such devices, typically encapsulated, utilize semiconductor memory devices or chips to store information and an antenna to send and receive data in the form of radio or high-frequency signals. The RFD system computer, or other device, could read the memory of an animals data tag using, for example, radio signals or high-frequency signals. Detailed testing information, as described above, may be output to and stored in such "local" memory to facilitate trending of limb movement data, or other variables, such as but not limited to weight. In such a configuration, the system would perform a read operation on the animal's data tag upon entry of the animal into the RFD. The animal's previous test data could be uploaded into the RFD computer and, following the movement of the animal through the RFD, could be compared to the current test data in various manners such as, but not limited to, those described above. Upon exit of the animal from the RFD, current test data could overwrite or supplement the previous test data in accord with data tag memory requirements. If memory is severely limited, the data tag may be advantageously used to simply store the results of previous test results. For example, if lameness is being detected and there is a 10-level severity scale, the date of a test and the severity on the 10-level scale could be saved in the data tag memory. In a subsequent test, that data could be retrieved to facilitate data analysis and trending in view of the new test results. Presently, the tags may be read from and written to several feet away within less than one second. Naturally, if the animal receives treatment, the data tag memory could be reset or supplemented with such information.

Figure 10:
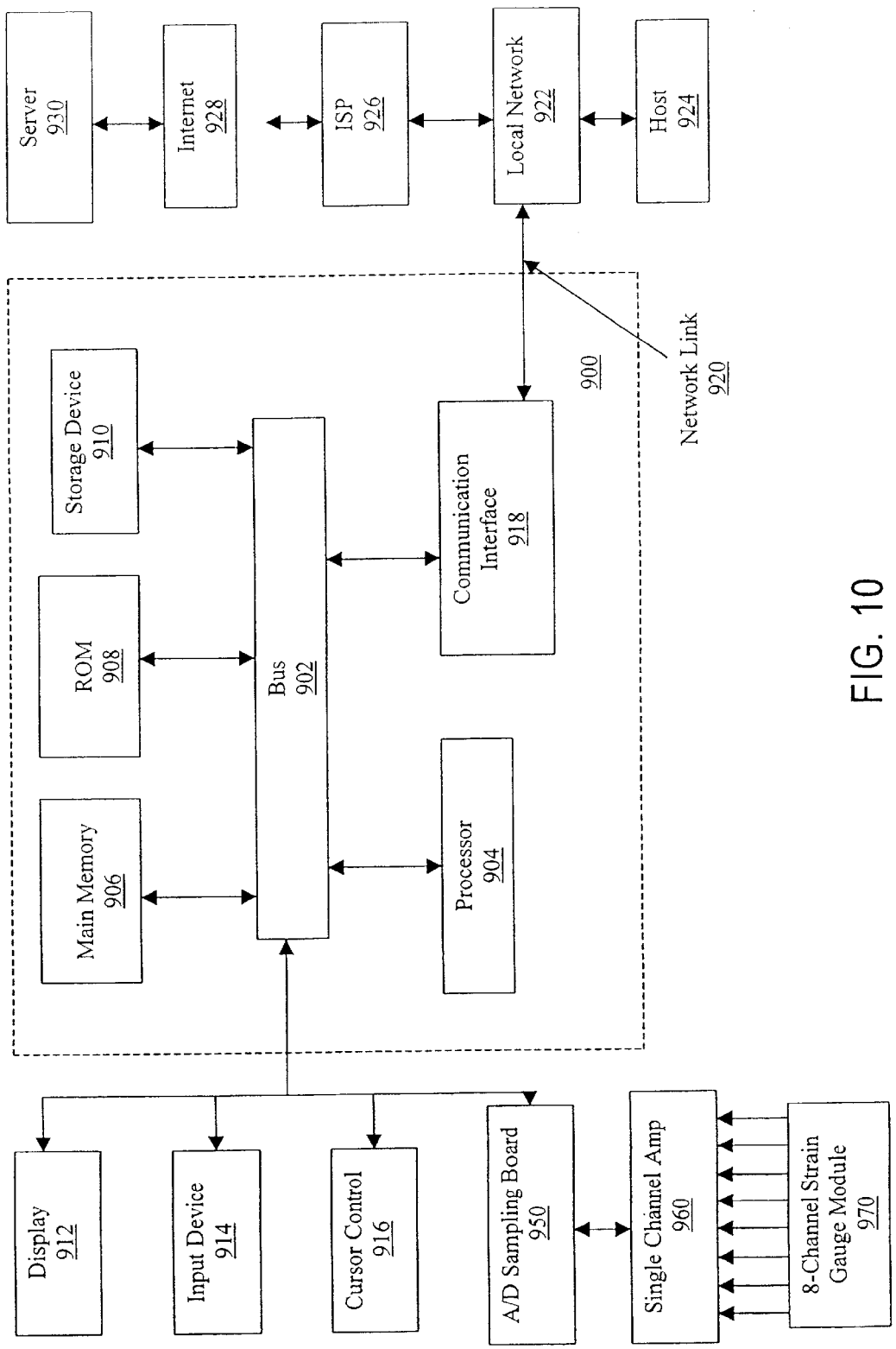
FIG. 10 depicts a computer-based system upon which the invention may be implemented.

Turning to the computer hardware executing the aforementioned data acquisition software and calibration program, FIG. 10 is a block diagram illustrating a conventional computer system 900 upon which an embodiment of the invention may be implemented. Computer system 900 includes a bus 902 or other communication mechanism for communicating information, and a processor or processors 904 coupled with bus 902 for processing information. Computer system 900 also includes a main memory 906, such as a random access memory (RAM) or other dynamic storage device, coupled to bus 902 for storing information and instructions to be executed by processor 904. Main memory 906 also may be used for storing temporary variables or other intermediate information during execution of instructions to be executed by processor 904. Computer system 900 further includes a read only memory (ROM) 908 or other static storage device coupled to bus 902 for storing static information and instructions for processor 904. A storage device 910, such as a magnetic disk or optical disk, is provided and coupled to bus 902 for storing information and instructions.

Computer system 900 may be coupled via bus 902 to a display 912, such as a cathode ray tube (CRT), for displaying information to a computer user. An input device 914, including alphanumeric and other keys, is coupled to bus 902 for communicating information and command selections to processor 904. Another type of user input device is cursor control 916, such as a mouse, a trackball, or cursor direction keys for communicating direction information and command selections to processor 904 and for controlling cursor movement on display 912. This input device typically has two degrees of freedom in two axes, a first axis (e.g., x) and a second axis (e.g., y), that allows the device to specify positions in a plane.

Computer system 900 is used to process all GRF data obtained by the various load cells by means of the calibration program and data acquisition software and converts the force data, using equations and principles discussed herein, into usable data. The pertinent programs and executable code is contained in main memory 906 and is selectively accessed and executed in response to processor 904, which executes one or more sequences of one or more instructions contained in main memory 906. Such instructions may be read into main memory 906 from another computer-readable medium, such as storage device 910. One or more processors in a multi-processing arrangement may also be employed to execute the sequences of instructions contained in main memory 906. In alternative embodiments, hard-wired circuitry may be used in place of or in combination with software instructions and it is to be understood that no specific combination of hardware circuitry and software are required.

The instructions may be provided in any number of forms such as source code, assembly code, object code, machine language, compressed or encrypted versions of the foregoing, and any and all equivalents thereof. "Computer-readable medium" refers to any medium that participates in providing instructions to processor 904 for execution and "program product" refers to such a computer-readable medium bearing a computer-executable program. The computer usable medium may be referred to as "bearing" the instructions, which encompass all ways in which instructions are associated with a computer usable medium.

Computer-readable mediums include, but are not limited to, non-volatile media, volatile media, and transmission media. Non-volatile media include, for example, optical or magnetic disks, such as storage device 910. Volatile media include dynamic memory, such as main memory 906. Transmission media include coaxial cables, copper wire and fiber optics, including the wires that comprise bus 902. Transmission media may comprise acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 904 for execution. For example, the instructions may initially be borne on a magnetic disk of a remote computer. The remote computer can load the instructions into its dynamic memory and send the instructions over a telephone line using a modem. A modem local to computer system 900 can receive the data on the telephone line and use an infrared transmitter to convert the data to an infrared signal. An infrared detector coupled to bus 902 can receive the data carried in the infrared signal and place the data on bus 902. Bus 902 carries the data to main memory 906, from which processor 904 retrieves and executes the instructions. The instructions received by main memory 906 may optionally be stored on storage device 910 either before or after execution by processor 104.

Computer system 900 may also include a communication interface 918 coupled to bus 902 to provide a two-way data communication coupling to a network link 920 connected to a local network 922. For example, communication interface 918 may be an integrated services digital network (ISDN) card or a modem to provide a data communication connection to a corresponding type of telephone line. As another example, communication interface 918 may be a local area network (LAN) card to provide a data communication connection to a compatible LAN. Wireless links may also be implemented. In any such implementation, communication interface 918 sends and receives electrical, electromagnetic or optical signals that carry digital data streams representing various types of information.

Network link 920 typically provides data communication through one or more networks to other data devices. For example, network link 920 may provide a connection through local network 922 to a host computer 924 or to data equipment operated by an Internet Service Provider (ISP) 926. ISP 926 in turn provides data communication services through the worldwide packet data communication network, now commonly referred to as the "Internet" 928. Local network 922 and Internet 928 both use electrical, electromagnetic or optical signals that carry digital data streams. The signals through the various networks and the signals on network link 920 and through communication interface 918, which carry the digital data to and from computer system 900, are exemplary forms of carrier waves transporting the information. Thus the processing required by method of the invention described by way of example herein may be implemented on a local computer utilizing storage device 910 or may be implemented, for example, on a LAN or over the internet.

Computer system 900 can send messages and receive data, including program code, through the network(s), network link 920, and communication interface 918. In the Internet example, a server 930 might transmit a requested code for an application program through Internet 928, ISP 926, local network 922 and communication interface 918. The received code may be executed by processor 904 as it is received, and/or stored in storage device 910, or other non-volatile storage for later execution. In this manner, computer system 900 may obtain application code in the form of a carrier wave.

While this invention has been described in connection with what is presently considered to be the most practical and preferred embodiment, it is to be understood that the invention is not limited to the disclosed aspects of the invention, but on the contrary, is intended to cover various modifications and equivalent arrangements included within the spirit and scope of the appended claims and may include modifications to such as, but not limited to, modification of the force plate geometry and adjustment of the number and placement of load cells to accommodate the monitored activity.

We claim:

1. A computer-based diagnostic system to detect and analyze ground reaction forces produced by an animal passing through the diagnostic system, comprising:

a first plate arranged on one side of the diagnostic system, said one side corresponding to one of a left and a right side of an animal and extending in a direction of travel of the animal;

a second plate arranged on another side of the diagnostic system, said another side corresponding to another one of a left and a right side of an animal and extending in a direction of travel of the animal, said second plate being disposed adjacent the first plate;

a first plurality of load cells, each of the first plurality of load cells configured to detect a force applied to the first plate along at least one axis and output a signal representative of the detected force;

a second plurality of load cells, each of the second plurality of load cells configured to detect a force applied to the second plate along at least one axis and output a signal representative of the detected force; and a processor adapted to execute at least one force analysis instruction set, wherein the force analysis instruction set receives the signals output from the first and second plurality of load cells and calculates, in combination with the processor, a magnitude and location of a force applied to both the first plate and the second plate, and wherein a length each of the first plate and the second plate is selected to be greater than a distance traversed by the animal at a standard walking gait of the animal so that each limb of the animal contacts a respective one of the first plate and second plate a plurality of times.

2. A computer-based diagnostic system to detect and analyze ground reaction forces produced by an animal passing through the diagnostic system, comprising:

a first plate arranged on one side of the diagnostic system, said one side corresponding to one of a left and a right side of an animal and extending in a direction of travel of the animal;

a second plate arranged on another side of the diagnostic system, said another side corresponding to another one of a left and a right side of an animal and extending in a direction of travel of the animal, said second plate being disposed adjacent the first plate;

a first plurality of load cells, each of the first plurality of load cells configured to detect a force applied to the first plate along at least one axis and output a signal representative of the detected force;

a second plurality of load cells, each of the second plurality of load cells configured to detect a force applied to the second plate along at least one axis and output a signal representative of the detected force; and a processor adapted to execute at least one force analysis instruction set, wherein the force analysis instruction set receives the signals output from the first and second plurality of load cells and calculates, in combination with the processor, a magnitude and location of a force applied to both the first plate and the second plate, and wherein a length of each of the first plate and the second plate is between about 150 to 500 cm, and wherein a width of each of the first plate and the second plate is between about 50 to 150 cm.

3. A computer-based diagnostic system to detect and analyze ground reaction forces produced by an animal passing through the diagnostic system, comprising:

a first plate arranged on one side of the diagnostic system, said one side corresponding to one of a left and a right side of an animal and extending in a direction of travel of the animal;

a second plate arranged on another side of the diagnostic system, said another side corresponding to another one of a left and a right side of an animal and extending in a direction of travel of the animal, said second plate being disposed adjacent the first plate;

a first plurality of load cells, each of the first plurality of load cells configured to detect a force applied to the first plate along at least one axis and output a signal representative of the detected force;

a second plurality of load cells, each of the second plurality of load cells configured to detect a force applied to the second plate along at least one axis and output a signal representative of the detected force; and a processor adapted to execute at least one force analysis instruction set, wherein the force analysis instruction set receives the signals output from the first and second plurality of load cells and calculates, in combination with the processor, a magnitude and location of a force applied to both the first plate and the second plate, and wherein a length each of the first plate and the second plate is selected to be greater than a distance traversed by the animal at a standard walking gait of the animal so that each limb of the animal contacts a respective one of the first plate and second plate at least once.

4. A computer-based diagnostic system to detect and analyze ground reaction forces produced by an animal passing through the diagnostic system in accord with claim 3, wherein the first plate and the second plate are disposed within a floor so that the surface of the first plate and the second plate are substantially level with a surface of the floor.

5. A computer-based diagnostic system to detect and analyze ground reaction forces produced by an animal passing through the diagnostic system in accord with claim 3, further comprising:

a step-up disposed at a proximal side of the first plate and the second plate;

a ramp down disposed at a distal side of first plate and the second plate.

6. A computer-based diagnostic system to detect and analyze ground reaction forces produced by an animal passing through the diagnostic system in accord with claim 5, further comprising:

a railing disposed on each side of the step-up, adjacent an outside side of the first plate, adjacent an outermost side of the second plate, and on each side of the ramp down;

an upwardly projecting divider disposed between the first plate and the second plate.

7. A computer-based diagnostic system to detect and analyze ground reaction forces produced by an animal passing through the diagnostic system in accord with claim 3, wherein said force analysis instruction comprises instructions which, when executed by the processor, compute a magnitude of the force applied to the first plate by summing the signals output by the first plurality of load cells, and wherein said force analysis instruction set comprises instructions which, when executed by the processor, compute a magnitude of the force applied to the second plate by summing the signals output by the second plurality of load cells.

8. A computer-based diagnostic system to detect and analyze ground reaction forces produced by an animal passing through the diagnostic system in accord with claim 7, wherein the force analysis instruction set comprises instructions which, when executed by the processor, compute a total force applied to at least one of the first plate and second plate by summing the magnitudes of forces applied to a respective one of the first and second plates.

9. A computer-based diagnostic system to detect and analyze ground reaction forces produced by an animal passing through the diagnostic system in accord with claim 8, wherein the force analysis instruction set comprises instructions which, when executed by the processor, compute a weight of the animal passing through the system by summing the magnitudes of forces applied to the first plate and the second plate.

10. A computer-based diagnostic system to detect and analyze ground reaction forces produced by an animal passing through the diagnostic system in accord with claim 9, wherein the force analysis instruction set comprises instructions which, when executed by the processor, compute a position of the force applied to at least one of the first plate and the second plate.

11. A computer-based diagnostic system to detect and analyze ground reaction forces produced by an animal passing through the diagnostic system in accord with claim 10, wherein the force analysis instruction set comprises instructions for determining a position of the force along at least one of an X-axis, Y-axis, and Z-axis by summing moments and forces along respective axes to solve n equations in n unknowns, where n is an integer.

12. A computer-based diagnostic system to detect and analyze ground reaction forces produced by an animal passing through the diagnostic system in accord with claim 11, wherein the force analysis instruction set comprises instructions which, when executed by the processor, compute an understep value for at least one side of the animal by calculating a difference between a position at which a fore limb applies a force to one of the first and second plates and a position at which a hind limb on the same side of the animal applies a force to the same plate.

13. A computer-based diagnostic system to detect and analyze ground reaction forces produced by an animal passing through the diagnostic system in accord with claim 12, wherein the force analysis instruction set comprises instructions which, when executed by the processor, compute the m-energy applied to the first plate or second plate by a limb of the animal by integrating a magnitude of the applied force to the first plate or second plate with respect to a frequency in a frequency domain.

14. A computer-based diagnostic system to detect and analyze ground reaction forces produced by an animal passing through the diagnostic system in accord with claim 12, wherein the force analysis instruction set comprises instructions which, when executed by the processor,
compute a first m-energy applied to one of the first and second plate by a fore limb of the animal by integrating a magnitude of the applied force to the plate with respect to a frequency in a frequency domain, and
compute a second m-energy applied to one of the first and second plate by a hind limb of the animal by integrating a magnitude of the applied force to the plate with respect to a frequency in a frequency domain.

15. A computer-based diagnostic system to detect and analyze ground reaction forces produced by an animal passing through the diagnostic system in accord with claim 12, wherein the force analysis instruction set comprises instructions which, when executed by the processor, compute the p-energy by taking the product of a magnitude of a force applied to the first plate or second plate by a limb of the animal and frequency integrated over a frequency domain.

16. A computer-based diagnostic system to detect and analyze ground reaction forces produced by an animal passing through the diagnostic system in accord with claim 12, wherein the force analysis instruction set comprises instructions which, when executed by the processor,
compute a first p-energy by taking the product of a magnitude of a force applied to the first plate or second plate by a fore limb of the animal and frequency integrated over a frequency domain; and
compute a second p-energy by taking the product of a magnitude of a force applied to the first plate or second plate by a hind limb of the animal and frequency integrated over a frequency domain.

17. A computer-based diagnostic system to detect and analyze ground reaction forces produced by an animal passing through the diagnostic system in accord with claim 11, wherein position of the force applied to at least one of the first plate and the second plate is computed as a function of time.

18. A computer-based diagnostic system to detect and analyze ground reaction forces produced by an animal passing through the diagnostic system in accord with claim 17, wherein the force analysis instruction set comprises instructions which, when executed by the processor, compute a peak normalized ground reaction force variable for at least one of the first plate and second plate by dividing the force applied to a respective one of the first plate and second plate by the weight of the animal.

19. A computer-based diagnostic system to detect and analyze ground reaction forces produced by an animal passing through the diagnostic system in accord with claim 18, wherein the force analysis instruction set comprises instructions which, when executed by the processor, compute a first peak normalized ground reaction force variable for the animal's fore limbs and a second peak normalized ground reaction force variable for the animal's hind limbs by dividing the force applied to a respective one of the animal's fore limbs and hind limbs by the weight of the animal.

20. A computer-based diagnostic system to detect and analyze ground reaction forces produced by an animal passing through the diagnostic system in accord with claim 19, wherein the force analysis instruction set comprises instructions which, when executed by the processor, compute a first impulse variable for a force applied to the first plate or the second plate by the animal's fore limbs and a second impulse variable for a force applied the first plate or the second plate by the animal's hind limbs, wherein each of the first and second impulse variable is calculated by integrating the normalized ground reaction force value with respect to the duration of application of each force to a respective plate and a second impulse variable for a force applied.

21. A computer-based diagnostic system to detect and analyze ground reaction forces produced by an animal passing through the diagnostic system in accord with claim 18, wherein the force analysis instruction set comprises instructions which, when executed by the processor, compute an impulse variable for each force applied to the first plate or the second plate by integrating the normalized ground reaction force value with respect to the duration of application of each force to a respective plate.

22. A computer-based diagnostic system to detect and analyze ground reaction forces produced by an animal passing through the diagnostic system in accord with claim 21, wherein the force analysis instruction set comprises instructions which, when executed by the processor, compute a stance time variable by calculating a total time that a limb is in contact with the first plate or second plate.

23. A computer-based diagnostic system to detect and analyze ground reaction forces produced by an animal passing through the diagnostic system in accord with claim 22,
wherein the force analysis instruction set comprises instructions which, when executed by the processor, compute the total time that a limb is in contact with the first plate or second plate by calculating a difference between a first time at which an applied force exceeds a predetermined threshold force and a second time at which an applied force falls below the predetermined threshold force for a discrete force application event, and wherein the predetermined threshold force is between 0.0 and 5.0 lbf.

24. A computer-based diagnostic system to detect and analyze ground reaction forces produced by an animal passing through the diagnostic system in accord with claim 22, wherein the force analysis instruction set comprises instructions which, when executed by the processor, compute a normalized average ground reaction force variable by dividing the impulse variable by the stance time variable.

25. A computer-based diagnostic system to detect and analyze ground reaction forces produced by an animal passing through the diagnostic system in accord with claim 24, wherein the force analysis instruction set comprises instructions which, when executed by the processor, compute a speed of the animal using a signal output by a speed sensing device.

26. A computer-based diagnostic system to detect and analyze ground reaction forces produced by an animal passing through the diagnostic system in accord with claim 25, wherein the force analysis instruction set comprises instructions which, when executed by the processor, compute a step size of the animal by calculating a difference between a first position at which a limb applies a force to one of the first and second plates and a second position at which the same limb applies a force to the respective first or second plate along an axis of motion of the animal.

27. A computer-based diagnostic system to detect and analyze ground reaction forces produced by an animal passing through the diagnostic system in accord with claim 26, wherein the force analysis instruction set comprises instructions which, when executed by the processor, compute the product of the first impulse variable and the animal speed to obtain a first characteristic unit length and to compute the product of the second impulse variable and the animal speed to obtain a second characteristic unit length.

28. A computer-based diagnostic system to detect and analyze ground reaction forces produced by an animal passing through the diagnostic system in accord with claim 21, wherein the force analysis instruction set comprises instructions which, when executed by the processor, compute a first stance time variable for a fore limb and a second stance time variable for a rear limb by calculating a total time that a limb is in contact with the first plate or second plate.

29. A computer-based diagnostic system to detect and analyze ground reaction forces produced by an animal passing through the diagnostic system in accord with claim 28, wherein wherein the force analysis instruction set comprises instructions which, when executed by the processor, compute a first total time that a fore limb is in contact with the first plate or second plate by calculating a difference between a first time at which an applied force from the fore limb exceeds a predetermined threshold force and a second time at which the applied force from the fore limb falls below the predetermined threshold force thus defining a first discrete force application event; and compute a second total time that a rear limb is in contact with the first plate or second plate by calculating a difference between a first time at which an applied force from the rear limb exceeds a predetermined threshold force and a second time at which the applied force from the rear limb falls below the predetermined threshold force thus defining a second discrete force application event.

30. A computer-based diagnostic system to detect and analyze ground reaction forces produced by an animal passing through the diagnostic system in accord with claim 29, wherein the predetermined threshold force is between 0.0 and 5.0 lbf.

31. A computer-based diagnostic system to detect and analyze ground reaction forces produced by an animal passing through the diagnostic system in accord with claim 28, wherein the force analysis instruction set comprises instructions which, when executed by the processor, compute a first normalized average ground reaction force variable by dividing the impulse variable for a first applied force by the first stance time variable and compute a second normalized average ground reaction force variable by dividing the impulse variable for a second applied force by the second stance time variable.

32. A computer-based diagnostic system to detect and analyze ground reaction forces produced by an animal passing through the diagnostic system in accord with claim 31, wherein the force analysis instruction set comprises instructions which, when executed by the processor, compute a speed of the animal using a signal output by a speed sensing device.

33. A computer-based diagnostic system to detect and analyze ground reaction forces produced by an animal passing through the diagnostic system in accord with claim 32, wherein the force analysis instruction set comprises instructions which, when executed by the processor, compute the product of the impulse variable and the animal speed to obtain a characteristic unit length.

34. A computer-based diagnostic system to detect and analyze ground reaction forces produced by an animal passing through the diagnostic system in accord with claim 11, wherein the force analysis instruction set comprises instructions which, when executed by the processor, compute a symmetry factor indicative of a difference in a force applied to the first plate and a force applied to the second plate.

35. A computer-based diagnostic system to detect and analyze ground reaction forces produced by an animal passing through the diagnostic system in accord with claim 34, wherein the force analysis instruction set comprises instructions which, when executed by the processor, compute the symmetry factor by taking the dividend of a right limb movement variable minus a left limb movement variable on the numerator and a right limb movement variable plus a left limb movement variable on the denominator.

36. A computer-based diagnostic system to detect and analyze ground reaction forces produced by an animal passing through the diagnostic system in accord with claim 35, wherein the right limb movement variable and the left limb movement variable comprise a normalized peak ground reaction force.

37. A computer-based diagnostic system to detect and analyze ground reaction forces produced by an animal passing through the diagnostic system in accord with claim 35, wherein the right limb movement variable and the left limb movement variable each comprise an impulse variable.

38. A computer-based diagnostic system to detect and analyze ground reaction forces produced by an animal pasting through the diagnostic system in accord with claim 35, wherein the right limb movement variable and the left limb movement variable each comprise a stance variable.

39. A computer-based diagnostic system to detect and analyze ground reaction forces produced by an animal passing through the diagnostic system in accord with claim 35, wherein the right limb movement variable and the left limb movement variable each comprise a normalized average ground reaction force variable.

40. A computer-based diagnostic system to detect and analyze ground reaction forces produced by an animal passing through the diagnostic system in accord with claim 35, wherein the right limb movement variable and the left limb movement variable each comprise a step size variable.

41. A computer-based diagnostic system to detect and analyze ground reaction forces produced by an animal passing through the diagnostic system in accord with claim 35, wherein the right limb movement variable and the left limb movement variable each comprise an m-energy variable.

42. A computer-based diagnostic system to detect and analyze ground reaction forces produced by an animal passing through the diagnostic system in accord with claim 35, wherein the right limb movement variable and the left limb movement variable each comprise a p-energy variable.

43. A computer-based diagnostic system to detect and analyze ground reaction forces produced by an animal passing through the diagnostic system in accord with claim 11, wherein the force analysis instruction set comprises instructions which, when executed by the processor, compute a symmetry factor indicative of a difference in a force applied to one of the first plate and the second plate by a fore limb and a force applied to one of the first plate and the second plate by a hind limb.

44. A computer-based diagnostic system to detect and analyze ground reaction forces produced by an animal passing through the diagnostic system in accord with claim 43, wherein the force analysis instruction set comprises instructions which, when executed by the processor, compute the symmetry factor by taking the dividend of a fore limb movement variable minus a hind limb movement variable on the numerator and a fore limb movement variable plus a hind limb movement variable on the denominator.

45. A computer-based diagnostic system to detect and analyze ground reaction forces produced by an animal passing through the diagnostic system in accord with claim 44, wherein the fore limb movement variable and the hind limb movement variable comprise a normalized peak ground reaction force.

46. A computer-based diagnostic system to detect and analyze ground reaction forces produced by an animal passing through the diagnostic system in accord with claim 44, wherein the fore limb movement variable and the hind limb movement variable each comprise an impulse variable.

47. A computer-based diagnostic system to detect and analyze ground reaction forces produced by an animal passing through the diagnostic system in accord with claim 44, wherein the fore limb movement variable and the hind limb movement variable each comprise a stance variable.

48. A computer-based diagnostic system to detect and analyze ground reaction forces produced by an animal passing through the diagnostic system in accord with claim 44, wherein the fore limb movement variable and the hind limb movement variable each comprise a normalized average ground reaction force variable.

49. A computer-based diagnostic system to detect and analyze ground reaction forces produced by an animal passing through the diagnostic system in accord with claim 44, wherein the fore limb movement variable and the hind limb movement variable each comprise a step size variable.

50. A computer-based diagnostic system to detect and analyze ground reaction forces produced by an animal passing through the diagnostic system in accord with claim 44, wherein the fore limb movement variable and the hind limb movement variable each comprise an m-energy variable.

51. A computer-based diagnostic system to detect and analyze ground reaction forces produced by an animal passing through the diagnostic system in accord with claim 44, wherein the fore limb movement variable and the hind limb movement variable each comprise a p-energy variable.

52. A computer-based diagnostic system to detect and analyze ground reaction forces produced by an animal passing through the diagnostic system comprising:
   a first plate arranged on one side of the diagnostic system, said one side corresponding to one of a left and a right side of an animal and extending in a direction of travel of the animal;
   a second plate arranged on another side of the diagnostic system, said another side corresponding to another one of a left and a right side of an animal and extending in a direction of travel of the animal, said second plate being disposed adjacent the first plate;
   a first plurality of load cells, each of the first plurality of load cells configured to detect a force applied to the first plate along at least one axis and output a signal representative of the detected force;
   a second plurality of load cells, each of the second plurality of load cells configured to detect a force applied to the second plate along at least one axis and output a signal representative of the detected force; and
   a processor adapted to execute at least one force analysis instruction set,
   wherein the force analysis instruction set receives the signals output from the first and second plurality of load cells and calculates, in combination with the processor, a magnitude and location of a force applied to both the first plate and the second plate, and
   wherein a length of each of the first plate and the second plate is greater than 150 cm.

53. A computer-based diagnostic system to detect and analyze ground reaction forces produced by an animal passing through the diagnostic system in accord with claim 52, further comprising:
   a speed sensor to determine a speed of the animal passing through the diagnostic system,
   wherein the speed sensor is at least one of an optically-based and acoustic-based sensor.

54. A computer-based diagnostic system to detect and analyze ground reaction forces produced by an animal passing through the diagnostic system in accord with claim 53, wherein the speed sensor comprises a photo cell and a corresponding reflective element.

55. A computer-based diagnostic system to detect and analyze ground reaction forces produced by an animal passing through the diagnostic system in accord with claim 54, wherein the speed sensor comprises a plurality of photo cells disposed along a length of the first plate or the second plate.

56. A computer-based method for detecting and analyzing ground reaction forces produced by an animal, comprising the steps of:
   guiding an animal to move across an instrumented force-sensing floor comprising a left floor plate, a right floor plate, a plurality of left floor plate load cells configured to measure a force applied to the left floor plate by movement of the animal's left limbs across the left floor plate of the force-sensing floor and output a force proportioned signal, and a plurality of right floor plate load cells configured to measure a force applied to the right floor plate by movement of the animal's right limbs across the right floor plate of the force-sensing floor and output a force proportioned signal;

constraining at least one of the animal's lateral body movement and leg movement so that the animal's left limbs contact the left floor plate and the animal's right limbs contact the right floor plate as the animal moves across the force-sensing floor;

calculating forces applied to one left floor plate and to the right floor plate by summing the signals output by the left floor plate load cells and right floor plate load cells, respectively; and comparing the calculated forces to a range of forces indicative of at least one of a sound animal condition, an indeterminate animal condition, or a lame animal condition.

57. A computer-based method for detecting and analyzing ground reaction forces produced by an animal in accord with claim 56, further comprising the step of:

computing a weight of the animal passing through the system by summing the magnitudes of forces applied to the first floor plate and the second floor plate.

58. A computer-based method for detecting and analyzing ground reaction forces produced by an animal in accord with claim 56, further comprising the step of:

computing a position of the force applied to at least one of the first floor plate and the second floor plate.

59. A computer-based method for detecting and analyzing ground reaction forces produced by an animal in accord with claim 56, further comprising the step of:

computing a position of the force along at least one of an X-axis, Y-axis, and Z-axis by summing moments and forces along respective axes to solve n equations in n unknowns, where n is an integer.

60. A computer-based method for detecting and analyzing ground reaction forces produced by an animal in accord with claim 59, further comprising the step of:

computing a position of the force applied to at least one of the first floor plate and the second floor plate as a function of time.

61. A computer-based method for detecting and analyzing ground reaction forces produced by an animal in accord with claim 60, further comprising the step of:

computing a peak normalized ground reaction force variable for at least one of the first floor plate and second floor plate by dividing the force applied to a respective one of the first plate and second plate by the weight of the animal.

62. A computer-based method for detecting and analyzing ground reaction forces produced by an animal in accord with claim 60, further comprising the step of:

computing an impulse variable for each force applied to the first floor plate or the second floor plate by integrating the normalized ground reaction force value with respect to the duration of application of each force to a respective floor plate.

63. A computer-based method for detecting and analyzing ground reaction forces produced by an animal in accord with claim 62, further comprising the step of:

computing a stance time variable by calculating a total time that a limb is in contact with the first floor plate or second floor plate.

64. A computer-based method for detecting and analyzing ground reaction forces produced by an animal in accord with claim 63, further comprising the step of:

computing a normalized average ground reaction force variable by dividing the impulse variable by the stance time variable.

65. A computer-based method for detecting and analyzing ground reaction forces produced by an animal in accord with claim 62, further comprising the step of:

computing a speed of the animal using a signal output by a speed sensor.

66. A computer-based method for detecting and analyzing ground reaction forces produced by an animal in accord with claim 65, further comprising the step of:

computing a product of the impulse variable and the animal speed to obtain a characteristic unit length.

67. A computer-based method for detecting and analyzing ground reaction forces produced by an animal in accord with claim 62, further comprising the step of:

computing the step size of the animal by calculating a difference between a first position at which a limb applies a force to one of the first and second floor plates and a second position at which the same limb applies a force to the respective first or second floor plate along an axis of motion of the animal.

68. A computer-based method for detecting and analyzing ground reaction forces produced by an animal in accord with claim 60, further comprising the step of:

computing the total time that a limb is in contact with the first floor plate or second floor plate by calculating a difference between a first time at which an applied force exceeds a predetermined threshold force and a second time at which an applied force falls below the predetermined threshold force for a discrete force application event.

69. A computer-based method for detecting and analyzing ground reaction forces produced by an animal in accord with claim 68, wherein the predetermined threshold force is between 0.0 and 5.0 lbf.

70. A computer-based method for detecting and analyzing ground reaction forces produced by an animal in accord with claim 60, further comprising the step of:

computing an m-energy applied to the first plate or second plate by a limb of the animal by integrating a magnitude of the applied force to the first floor plate or second floor plate with respect to a frequency in a frequency domain.

71. A computer-based method for detecting and analyzing ground reaction forces produced by an animal in accord with claim 60, further comprising the step of:

computing a p-energy by taking the product of a magnitude of a force applied to the first floor plate or second floor plate by a limb of the animal and frequency integrated over a frequency domain.

72. A computer-based method for detecting and analyzing ground reaction forces produced by an animal in accord with claim 60, further comprising the step of:

computing a symmetry factor indicative of a difference in a force applied to the first plate and a force applied to the second plate.

73. A computer-based method for detecting and analyzing ground reaction forces produced by an animal in accord with claim 72, further comprising the step of:

computing a symmetry factor by taking the dividend of a right limb movement variable minus a left limb movement variable on the numerator and a right limb movement variable plus a left limb movement variable on the denominator.

74. A computer-based method for detecting and analyzing ground reaction forces produced by an animal in accord with claim 73, wherein the right limb movement variable and the left limb movement variable comprise a normalized peak ground reaction force.

75. A computer-based method for detecting and analyzing ground reaction forces produced by an animal in accord with claim 73, wherein the right limb movement variable and the left limb movement variable each comprise an impulse variable.

76. A computer-based method for detecting and analyzing ground reaction forces produced by an animal in accord with claim 73, wherein the right limb movement variable and the left limb movement variable each comprise a stance variable.

77. A computer-based method for detecting and analyzing ground reaction forces produced by an animal in accord with claim 73, wherein the right limb movement variable and the left limb movement variable each comprise a normalized average ground reaction force variable.

78. A computer-based method for detecting and analyzing ground reaction forces produced by an animal in accord with claim 73, wherein the right limb movement variable and the left limb movement variable each comprise a step size variable.

79. A computer-based method for detecting and analyzing ground reaction forces produced by an animal in accord with claim 73, wherein the right limb movement variable and the left limb movement variable each comprise an m-energy variable.

80. A computer-based method for detecting and analyzing ground reaction forces produced by an animal in accord with claim 73, wherein the right limb movement variable and the left limb movement variable each comprise a p-energy variable.

81. A computer-based method for detecting and analyzing ground reaction forces produced by an animal in accord with claim 72, further comprising the step of:
computing a symmetry factor by taking the dividend of a fore limb movement variable minus a hind limb movement variable on the numerator and a fore limb movement variable plus a hind limb movement variable on the denominator.

82. A computer-based method for detecting and analyzing ground reaction forces produced by an animal in accord with claim 81, wherein the fore limb movement variable and the hind limb movement variable comprise a normalized peak ground reaction force.

83. A computer-based method for detecting and analyzing ground reaction forces produced by an animal in accord with claim 81, wherein the fore limb movement variable and the hind limb movement variable each comprise an impulse variable.

84. A computer-based method for detecting and analyzing ground reaction forces produced by an animal in accord with claim 81, wherein the fore limb movement variable and the hind limb movement variable each comprise a stance variable.

85. A computer-based method for detecting and analyzing ground reaction forces produced by an animal in accord with claim 81, wherein the fore limb movement variable and the hind limb movement variable each comprise a normalized average ground reaction force variable.

86. A computer-based method for detecting and analyzing ground reaction forces produced by an animal in accord with claim 81, wherein the fore limb movement variable and the hind limb movement variable each comprise a step size variable.

87. A computer-based method for detecting and analyzing ground reaction forces produced by an animal in accord with claim 81, wherein the fore limb movement variable and the hind limb movement variable each comprise an m-energy variable.

88. A computer-based method for detecting and analyzing ground reaction forces produced by an animal in accord with claim 81, wherein the fore limb movement variable and the hind limb movement variable each comprise a p-energy variable.

89. A computer-readable medium bearing instructions enabling a computer having at least one processor to detect and analyze ground reaction forces produced by an animal to determine a physical condition of the animal, the instructions, when executed by a computer, causing the computer to carry out the steps of:
calculating ground reaction forces produced by the animal as it moves across a left floor plate and a right floor plate by summing the force proportioned signals output by load cells separately measuring loads of each of the left floor plate and the right floor plate caused by movement of the animal across the respective left floor plate and right floor plate; and
comparing the calculated forces corresponding to movement of the animal across the left floor plate and right floor plate to a range of forces indicative of at least one of a sound animal condition, an indeterminate animal condition, or a lame animal condition.

90. A computer-readable medium bearing instructions enabling a computer having at least one processor to detect and analyze ground reaction forces produced by an animal in accord with claim 89 to determine a physical condition of the animal, the instructions, when executed by a computer, causing the computer to carry out at least one of the steps of:
computing a weight of the animal passing through the system by summing the magnitudes of forces applied to the first floor plate and the second floor plate;
computing a position of the force applied to at least one of the first floor plate and the second floor plate;
computing a position of the force along at least one of an X-axis, Y-axis, and Z-axis by summing moments and forces along respective axes to solve n equations in n unknowns, where n is an integer;
computing an understep value for at least one side of the animal by calculating a difference between a position at which a fore limb applies a force to one of the first and second plates and a position at which a hind limb on the same side of the animal applies a force to the same plate;
computing a position of the force applied to at least one of the first floor plate and the second floor plate as a function of time;
computing a peak normalized ground reaction force variable for at least one of the first floor plate and second floor plate by dividing the force applied to a respective one of the first plate and second plate by the weight of the animal;
computing an impulse variable for each force applied to the first floor plate or the second floor plate by integrating the normalized ground reaction force value with respect to the duration of application of each force to a respective floor plate;
computing a stance time variable by calculating a total time that a limb is in contact with the first floor plate or second floor plate;
computing the total time that a limb is in contact with the first floor plate or second floor plate by calculating a difference between a first time at which an applied force exceeds a predetermined threshold force and a second time at which an applied force falls below the a predetermined threshold force between about 0.0 and 5.0 lbf for a discrete force application event;

computing a normalized average ground reaction force variable by dividing the impulse variable by the stance time variable;

computing a speed of the animal using a signal output by a speed sensor;

computing the step size of the animal by calculating a difference between a first position at which a limb applies a force to one of the first and second floor plates and a second position at which the same limb applies a force to the respective first or second floor plate along an axis of motion of the animal, computing a product of the impulse variable and the animal speed to obtain a characteristic unit length;

computing an m-energy applied to the first plate or second plate by a limb of the animal by integrating a magnitude of the applied force to the first floor plate or second floor plate with respect to a frequency in a frequency domain; and computing a p-energy by taking the product of a magnitude of a force applied to the first floor plate or second floor plate by a limb of the animal and frequency integrated over a frequency domain.

91. A computer-readable medium bearing instructions enabling a computer having at least one processor to detect and analyze ground reaction forces produced by an animal in accord with claim 90 to determine a physical condition of the animal, the instructions, when executed by a computer, causing the computer to carry out the step of:

computing a symmetry factor indicative of a difference in a force applied to one of the first plate and the second plate by a fore limb and a force applied to the same one of the first plate and the second plate by a hind limb.

92. A computer-readable medium bearing instructions enabling a computer having at least one processor to detect and analyze ground reaction forces produced by an animal in accord with claim 90 to determine a physical condition of the animal, the instructions, when executed by a computer, causing the computer to carry out the step of:

computing a symmetry factor indicative of a difference in a force applied to the first plate and a force applied to the second plate.

93. A computer-readable medium bearing instructions enabling a computer having at least one processor to detect and analyze ground reaction forces produced by an animal in accord with claim 92 to determine a physical condition of the animal, the instructions, when executed by a computer, causing the computer to carry out the step of:

computing a symmetry factor by taking the dividend of a right limb movement variable minus a left limb movement variable on the numerator and a right limb movement variable plus a left limb movement variable on the denominator.

94. A computer-readable medium bearing instructions enabling a computer having at least one processor to detect and analyze ground reaction forces produced by an animal in accord with claim 93, wherein the right limb movement variable and the left limb movement variable comprise one of a normalized peak ground reaction force, an impulse variable, a stance variable, a normalized average ground reaction force variable, a step size variable, an m-energy variable, and a p-energy variable.

* * * * *